United States Patent
Wilson et al.

(10) Patent No.: US 9,833,316 B2
(45) Date of Patent: *Dec. 5, 2017

(54) TRANS-APICAL IMPLANT SYSTEMS, IMPLANTS AND METHODS

(71) Applicant: Cardiosolutions, Inc., West Bridgewater, MA (US)

(72) Inventors: Jonathan E. Wilson, Mattapoisett, MA (US); Jack Robertson, Abington, MA (US); Christopher Seguin, Norton, MA (US); John Murphy, Plymouth, MA (US)

(73) Assignee: CARDIOSOLUTIONS, INC., West Bridgewater, MA (US)

( * ) Notice: Subject to any disclaimer, the term of this patent is extended or adjusted under 35 U.S.C. 154(b) by 83 days.

This patent is subject to a terminal disclaimer.

(21) Appl. No.: 14/962,729

(22) Filed: Dec. 8, 2015

(65) Prior Publication Data

US 2016/0089237 A1  Mar. 31, 2016

Related U.S. Application Data

(63) Continuation of application No. 13/838,752, filed on Mar. 15, 2013, now Pat. No. 9,232,998.

(51) Int. Cl.
*A61F 2/24* (2006.01)
*A61B 17/00* (2006.01)
*A61B 17/34* (2006.01)

(52) U.S. Cl.
CPC ............ *A61F 2/2433* (2013.01); *A61F 2/246* (2013.01); *A61F 2/2427* (2013.01);
(Continued)

(58) Field of Classification Search
CPC ...... A61F 2/2427; A61F 2/243; A61F 2/2433; A61F 2/246; A61F 2/2466
See application file for complete search history.

(56) References Cited

U.S. PATENT DOCUMENTS

| | | | |
|---|---|---|---|
| 2,625,967 A | 1/1953 | Stull | |
| 2,549,731 A | 4/1954 | Wattley | |

(Continued)

FOREIGN PATENT DOCUMENTS

| | | | |
|---|---|---|---|
| CN | 1961983 A | 5/2007 | |
| CN | 101484093 A | 7/2009 | |

(Continued)

OTHER PUBLICATIONS

Acar et al., AREVA: Multicenter Randomized Comparison of Low-Dose Versus Standard-Dose Anticoagulation in Patients With Mechanical Prosthetic Heart Valves, Circulation, Nov. 1, 1996, 2107-12, vol. 94, No. 9.

(Continued)

*Primary Examiner* — Ryan J Severson
(74) *Attorney, Agent, or Firm* — Reza Mollaaghababa; Thomas J. Engellenner; Pepper Hamilton LLP

(57) ABSTRACT

A trans-apical implant includes a spacer defining spacer cavity configured to be expanded from a retracted position, a shaft extending from the spacer, the shaft defining an inflation lumen fluidly coupled to the spacer cavity and configured to be fluidly coupled to an expansion medium source, and a spacer valve assembly disposed within at least one of the spacer or shaft, the spacer valve assembly configured to allow selectively allow an expansion medium to flow into the spacer cavity to be selectively expand the spacer from a retracted position to an expanded position.

19 Claims, 22 Drawing Sheets

(52) U.S. Cl.
CPC .. *A61F 2/2466* (2013.01); *A61B 2017/00243* (2013.01); *A61B 2017/00247* (2013.01); *A61B 2017/3425* (2013.01); *A61F 2250/0003* (2013.01)

(56) References Cited

U.S. PATENT DOCUMENTS

| | | |
|---|---|---|
| 3,197,788 A | 8/1965 | Segger |
| 3,445,916 A | 5/1969 | Schulte |
| 3,551,913 A | 1/1971 | Shiley et al. |
| 3,586,029 A | 6/1971 | Evers |
| 3,589,392 A | 6/1971 | Meyer |
| 3,671,979 A | 6/1972 | Moulopoulos |
| 3,689,942 A | 9/1972 | Rapp |
| 3,714,671 A | 2/1973 | Edwards et al. |
| 3,739,402 A | 6/1973 | Cooley et al. |
| 3,983,581 A | 10/1976 | Angell et al. |
| 4,079,468 A | 3/1978 | Liotta et al. |
| 4,084,268 A | 4/1978 | Ionescu et al. |
| 4,246,893 A | 1/1981 | Berson |
| 4,259,753 A | 4/1981 | Liotta et al. |
| 4,291,420 A | 9/1981 | Reul |
| 4,297,749 A | 11/1981 | Davis et al. |
| 4,439,185 A | 3/1984 | Lundquist |
| 4,535,757 A | 8/1985 | Webster, Jr. |
| 4,597,767 A | 7/1986 | Lenkei |
| 4,836,204 A | 6/1989 | Landymore et al. |
| 4,865,030 A | 9/1989 | Polyak |
| 4,960,424 A | 10/1990 | Grooters |
| 5,002,067 A | 3/1991 | Berthelsen et al. |
| 5,217,484 A | 6/1993 | Marks |
| 5,222,973 A | 6/1993 | Sharpe et al. |
| 5,261,916 A | 11/1993 | Engelson |
| 5,304,195 A | 4/1994 | Twyford, Jr. et al. |
| 5,308,357 A | 5/1994 | Lichtman |
| 5,318,589 A | 6/1994 | Lichtman |
| 5,350,397 A | 9/1994 | Palermo et al. |
| 5,397,351 A | 3/1995 | Pavcnik et al. |
| 5,411,552 A | 5/1995 | Andersen et al. |
| 5,415,667 A | 5/1995 | Frater |
| 5,462,527 A | 10/1995 | Stevens-Wright et al. |
| 5,509,428 A | 4/1996 | Dunlop |
| 5,554,185 A | 9/1996 | Block et al. |
| 5,582,607 A | 12/1996 | Lackman |
| 5,611,800 A | 3/1997 | Davis et al. |
| 5,634,936 A | 6/1997 | Linden et al. |
| 5,638,827 A | 6/1997 | Palmer et al. |
| 5,649,949 A | 7/1997 | Wallace et al. |
| 5,653,712 A | 8/1997 | Stern |
| 5,665,100 A | 9/1997 | Yoon |
| 5,713,954 A | 2/1998 | Rosenberg et al. |
| 5,776,075 A | 7/1998 | Palmer |
| 5,792,179 A | 8/1998 | Sideris |
| 5,797,958 A | 8/1998 | Yoon |
| 5,814,098 A | 9/1998 | Hinnenkamp et al. |
| 5,840,081 A | 11/1998 | Andersen et al. |
| 5,891,130 A | 4/1999 | Palermo et al. |
| 5,895,391 A | 4/1999 | Farnholtz |
| 5,928,224 A | 7/1999 | Laufer |
| 5,957,865 A | 9/1999 | Backman et al. |
| 5,957,949 A | 9/1999 | Leonhardt et al. |
| 5,964,806 A | 10/1999 | Cook et al. |
| 5,989,242 A | 11/1999 | Saadat et al. |
| 5,993,474 A | 11/1999 | Ouchi |
| 6,090,096 A | 7/2000 | St. Goar et al. |
| 6,152,144 A | 11/2000 | Lesh et al. |
| 6,168,614 B1 | 1/2001 | Andersen et al. |
| 6,183,512 B1 | 2/2001 | Howanec et al. |
| 6,190,373 B1 | 2/2001 | Palermo et al. |
| 6,217,610 B1 | 4/2001 | Carpentier et al. |
| 6,283,127 B1 | 9/2001 | Sterman et al. |
| 6,283,995 B1 | 9/2001 | Moe et al. |
| 6,287,339 B1 | 9/2001 | Vazquez et al. |
| 6,332,893 B1 | 12/2001 | Mortier et al. |
| 6,358,277 B1 | 3/2002 | Duran |
| 6,406,420 B1 | 6/2002 | McCarthy et al. |
| 6,415,693 B1 | 7/2002 | Simon et al. |
| 6,416,549 B1 | 7/2002 | Chinn et al. |
| 6,419,695 B1 | 7/2002 | Gabbay |
| 6,440,132 B1 | 8/2002 | Jackson |
| 6,454,798 B1 | 9/2002 | Moe |
| 6,461,382 B1 | 10/2002 | Cao |
| 6,482,228 B1 | 11/2002 | Norred |
| 6,508,825 B1 | 1/2003 | Selmon et al. |
| 6,517,515 B1 | 2/2003 | Eidenschink |
| 6,592,606 B2 | 7/2003 | Huter et al. |
| 6,629,534 B1 | 10/2003 | St. Goar et al. |
| 6,652,578 B2 | 11/2003 | Bailey et al. |
| 6,673,100 B2 | 1/2004 | Diaz et al. |
| 6,682,559 B2 | 1/2004 | Myers et al. |
| 6,695,866 B1 | 2/2004 | Kuehn et al. |
| 6,746,404 B2 | 6/2004 | Schwartz |
| 6,764,510 B2 | 7/2004 | Vidlund et al. |
| 6,767,362 B2 | 7/2004 | Schreck |
| 6,769,434 B2 | 8/2004 | Liddicoat et al. |
| 6,805,711 B2 | 10/2004 | Quijano et al. |
| 6,821,297 B2 | 11/2004 | Snyders |
| 6,830,584 B1 | 12/2004 | Seguin |
| 6,830,585 B1 | 12/2004 | Artoff et al. |
| 6,849,081 B2 | 2/2005 | Sepetka et al. |
| 6,869,444 B2 | 3/2005 | Gabbay |
| 6,896,700 B2 | 5/2005 | Lu et al. |
| 6,911,043 B2 | 6/2005 | Myers et al. |
| 6,964,684 B2 | 11/2005 | Ortiz et al. |
| 6,971,998 B2 | 12/2005 | Rosenman et al. |
| 6,974,476 B2 | 12/2005 | McGuckin, Jr. et al. |
| 6,976,950 B2 | 12/2005 | Connors et al. |
| 7,018,406 B2 | 3/2006 | Seguin et al. |
| 7,056,286 B2 | 6/2006 | Ravenscroft et al. |
| 7,070,618 B2 | 7/2006 | Streeter |
| 7,077,862 B2 | 7/2006 | Vidlund et al. |
| 7,101,395 B2 | 9/2006 | Tremulis et al. |
| 7,112,219 B2 | 9/2006 | Vidlund et al. |
| 7,160,322 B2 | 1/2007 | Gabbay |
| 7,189,199 B2 | 3/2007 | McCarthy et al. |
| 7,247,134 B2 | 7/2007 | Vidlund et al. |
| 7,335,213 B1 | 2/2008 | Hyde et al. |
| 7,344,553 B2 | 3/2008 | Opolski et al. |
| 7,374,572 B2 | 5/2008 | Gabbay |
| 7,381,210 B2 | 6/2008 | Zarbatany et al. |
| 7,404,824 B1 | 7/2008 | Webler et al. |
| 7,657,326 B2 | 2/2010 | Bodner et al. |
| 7,678,145 B2 | 3/2010 | Vidlund et al. |
| 7,704,268 B2 | 4/2010 | Chanduszko |
| 7,753,949 B2 | 7/2010 | Lamphere et al. |
| 7,785,366 B2 | 8/2010 | Maurer et al. |
| 7,927,370 B2 | 4/2011 | Webler et al. |
| 7,942,928 B2 | 5/2011 | Webler et al. |
| 7,963,973 B2 | 6/2011 | Nguyen et al. |
| 8,092,525 B2 | 1/2012 | Eliasen et al. |
| 8,118,822 B2 | 2/2012 | Schaller et al. |
| 8,216,302 B2 | 7/2012 | Wilson et al. |
| 8,486,136 B2 | 7/2013 | Maurer et al. |
| 8,506,623 B2 | 8/2013 | Wilson et al. |
| 2001/0007956 A1 | 7/2001 | Letac et al. |
| 2001/0010017 A1 | 7/2001 | Cribier et al. |
| 2001/0018611 A1 | 8/2001 | Solem et al. |
| 2002/0029080 A1 | 3/2002 | Mortier et al. |
| 2002/0032480 A1 | 3/2002 | Spence et al. |
| 2002/0042651 A1 | 4/2002 | Liddicoat et al. |
| 2002/0058995 A1 | 5/2002 | Stevens |
| 2002/0077566 A1 | 6/2002 | Laroya et al. |
| 2002/0081553 A1 | 6/2002 | Tramonte |
| 2002/0169377 A1 | 11/2002 | Khairkhahan et al. |
| 2002/0169502 A1 | 11/2002 | Mathis |
| 2002/0183838 A1 | 12/2002 | Liddicoat et al. |
| 2002/0188170 A1 | 12/2002 | Santamore et al. |
| 2003/0033009 A1 | 2/2003 | Gabbay |
| 2003/0040792 A1 | 2/2003 | Gabbay |
| 2003/0105519 A1 | 6/2003 | Fasol et al. |
| 2003/0120264 A1 | 6/2003 | Lattouf |
| 2003/0130731 A1 | 7/2003 | Vidlund et al. |
| 2003/0139751 A1 | 7/2003 | Evans et al. |
| 2003/0144574 A1 | 7/2003 | Heilman et al. |

(56) References Cited

U.S. PATENT DOCUMENTS

| | | |
|---|---|---|
| 2003/0181945 A1 | 9/2003 | Opolski et al. |
| 2003/0199975 A1 | 10/2003 | Gabbay |
| 2003/0208203 A1 | 11/2003 | Lim et al. |
| 2003/0212453 A1 | 11/2003 | Mathis et al. |
| 2004/0034366 A1 | 2/2004 | van der Burg et al. |
| 2004/0044402 A1 | 3/2004 | Jung et al. |
| 2004/0088047 A1 | 5/2004 | Spence et al. |
| 2004/0106989 A1 | 6/2004 | Wilson et al. |
| 2004/0122512 A1 | 6/2004 | Navia et al. |
| 2004/0127981 A1 | 7/2004 | Rahdert et al. |
| 2004/0127983 A1 | 7/2004 | Mortier et al. |
| 2004/0148019 A1 | 7/2004 | Vidlund et al. |
| 2004/0148020 A1 | 7/2004 | Vidlund et al. |
| 2004/0181256 A1 | 9/2004 | Glaser |
| 2004/0210304 A1 | 10/2004 | Seguin et al. |
| 2004/0210307 A1 | 10/2004 | Khairkhahan |
| 2004/0225353 A1 | 11/2004 | McGuckin, Jr. et al. |
| 2004/0225354 A1 | 11/2004 | Allen et al. |
| 2004/0243229 A1 | 12/2004 | Vidlund et al. |
| 2004/0260322 A1 | 12/2004 | Rudko et al. |
| 2005/0021056 A1 | 1/2005 | St. Goar et al. |
| 2005/0027337 A1 | 2/2005 | Rudko et al. |
| 2005/0033446 A1 | 2/2005 | Deem et al. |
| 2005/0038508 A1 | 2/2005 | Gabbay |
| 2005/0038509 A1 | 2/2005 | Ashe |
| 2005/0065591 A1 | 3/2005 | Moberg et al. |
| 2005/0070999 A1 | 3/2005 | Spence |
| 2005/0075727 A1 | 4/2005 | Wheatley |
| 2005/0090824 A1 | 4/2005 | Shluzas et al. |
| 2005/0131451 A1 | 6/2005 | Kleshinski et al. |
| 2005/0149182 A1 | 7/2005 | Alferness et al. |
| 2005/0159810 A1 | 7/2005 | Filsoufi |
| 2005/0222488 A1 | 10/2005 | Chang et al. |
| 2005/0229433 A1 | 10/2005 | Cachia |
| 2005/0288786 A1 | 12/2005 | Chanduszko |
| 2006/0020335 A1 | 1/2006 | Kowalsky et al. |
| 2006/0025855 A1 | 2/2006 | Lashinski et al. |
| 2006/0058871 A1 | 3/2006 | Zakay et al. |
| 2006/0084943 A1 | 4/2006 | Rosenman et al. |
| 2006/0129025 A1 | 6/2006 | Levine et al. |
| 2006/0149368 A1 | 7/2006 | Spence |
| 2006/0155326 A1 | 7/2006 | Aranyi |
| 2006/0178700 A1 | 8/2006 | Quinn |
| 2006/0195012 A1 | 8/2006 | Mortier et al. |
| 2006/0195185 A1 | 8/2006 | Lane et al. |
| 2006/0199995 A1 | 9/2006 | Vijay |
| 2006/0229708 A1 | 10/2006 | Powell et al. |
| 2006/0241745 A1 | 10/2006 | Solem |
| 2006/0253072 A1 | 11/2006 | Pai et al. |
| 2006/0293698 A1 | 12/2006 | Douk |
| 2007/0016286 A1 | 1/2007 | Herrmann et al. |
| 2007/0049980 A1 | 3/2007 | Zielinski et al. |
| 2007/0093890 A1 | 4/2007 | Eliasen et al. |
| 2007/0118151 A1 | 5/2007 | Davidson |
| 2007/0167981 A1 | 7/2007 | Opolski et al. |
| 2007/0185571 A1 | 8/2007 | Kapadia et al. |
| 2007/0198050 A1 | 8/2007 | Ravenscroft et al. |
| 2007/0198082 A1 | 8/2007 | Kapadia et al. |
| 2007/0213578 A1 | 9/2007 | Khairkhahan et al. |
| 2007/0232981 A1 | 10/2007 | Ravenscroft et al. |
| 2007/0232992 A1 | 10/2007 | Kutsko et al. |
| 2007/0239154 A1 | 10/2007 | Shaolian et al. |
| 2007/0255399 A1 | 11/2007 | Eliasen et al. |
| 2007/0265700 A1 | 11/2007 | Eliasen et al. |
| 2007/0282429 A1 | 12/2007 | Hauser et al. |
| 2007/0293943 A1 | 12/2007 | Quinn |
| 2008/0125860 A1 | 5/2008 | Webler et al. |
| 2008/0125861 A1 | 5/2008 | Webler et al. |
| 2008/0183105 A1 | 7/2008 | Greenhalgh et al. |
| 2008/0195200 A1 | 8/2008 | Vidlund et al. |
| 2008/0208329 A1 | 8/2008 | Bishop et al. |
| 2008/0288061 A1 | 11/2008 | Maurer et al. |
| 2009/0043382 A1 | 2/2009 | Maurer et al. |
| 2009/0048668 A1 | 2/2009 | Wilson et al. |
| 2009/0082874 A1 | 3/2009 | Cachia |
| 2009/0093670 A1 | 4/2009 | Annest et al. |
| 2009/0105814 A1 | 4/2009 | Groothuis et al. |
| 2009/0131849 A1 | 5/2009 | Maurer et al. |
| 2009/0131880 A1 | 5/2009 | Speziali et al. |
| 2009/0132033 A1 | 5/2009 | Maurer et al. |
| 2009/0163934 A1 | 6/2009 | Raschdorf, Jr. et al. |
| 2009/0240326 A1 | 9/2009 | Wilson et al. |
| 2010/0016655 A1 | 1/2010 | Annest et al. |
| 2010/0022948 A1 | 1/2010 | Wilson et al. |
| 2010/0324668 A1 | 12/2010 | Maurer et al. |
| 2012/0143320 A1 | 6/2012 | Eliasen et al. |
| 2013/0211513 A1 | 8/2013 | Rourke et al. |
| 2014/0277404 A1 | 9/2014 | Wilson et al. |
| 2014/0371843 A1 | 12/2014 | Wilson et al. |
| 2014/0371846 A1 | 12/2014 | Wilson et al. |
| 2015/0127097 A1 | 5/2015 | Neumann |

FOREIGN PATENT DOCUMENTS

| | | |
|---|---|---|
| EP | 1323438 | 2/2003 |
| EP | 0125393 | 8/2007 |
| GB | 1264472 | 2/1972 |
| GB | 1268484 | 3/1972 |
| GB | 1388064 | 3/1975 |
| WO | 8900030 A1 | 1/1989 |
| WO | WO 03049619 | 6/2003 |
| WO | 03096932 A1 | 11/2003 |
| WO | WO 2006032051 | 3/2006 |
| WO | WO 2006064490 | 6/2006 |
| WO | WO 2006091597 | 8/2006 |
| WO | WO 2006111391 | 10/2006 |
| WO | WO 2006127509 | 11/2006 |
| WO | WO 2007064810 | 6/2007 |
| WO | WO 2007078772 | 7/2007 |
| WO | WO 2007100409 | 9/2007 |
| WO | WO 2007140470 | 12/2007 |
| WO | WO 2008079828 | 7/2008 |
| WO | 2008141322 A1 | 11/2008 |
| WO | WO 2009053952 | 4/2009 |

OTHER PUBLICATIONS

Acker et al., Mitral valve surgery in heart failure: Insights from the Acorn Clinical Trial, Surgery for Acquired Cardiovascular Disease, The Journal of Thoracic and Cardiovascular Surgery, Sep. 2006, 568-577.e4, vol. 132, No. 3.

A first for MiCardia's Dynoplasty, Medical Device Daily, Feb. 19, 2009, vol. 13, No. 32, 1 page.

Babaliaros et al., Emerging Applications for Transseptal Left Heart Catheterization—Old Techniques for New Procedures, Journal of the American College of Cardiology, Jun. 3, 2008, 2116-22, vol. 51, No. 22.

Bailey, et al., "The Surgical Correction of Mitral Insufficiency by the Use of Pericardia! Grafts" Dec. 1954 (pp. 551-627).

Bailey, et al., "Surgical Repair of Mitral Insufficiency" Feb. 1951 (pp. 125-137).

Bailey, et al., "Closed Intracardiac Tactile Surgery" Jul. 1952 (pp. 1-24).

Balzer et al., Real-time transesophageal three-dimensional echocardiography for guidance of percutaneous cardiac interventions: first experience, Clinical Research in Cardiology, May 29, 2008, 565-574, vol. 97, No. 9.

Benichoux, et al., "A Method of Surgical Correction of Mitral Insufficiency" 1955 (pp. 148-158).

Blalock, "A Consideration of Some of the Problems in Cardiovascular Surgery" Jun. 1951 (pp. 543-571 ).

B-Lundqvist et al., Transseptal Left Heart Catheterization: A Review of 278 Studies, Clin. Cardiel., Jan. 1986, 21-26, vol. 9.

Bonow et al., ACC/AHA 2006 Guidelines for the Management of Patients With Valvular Heart Disease: Executive Summary, Circulation—Journal of the American Heart Association, Downloaded from circ.ahajournals.org, Jul. 31, 2008, 449-527.

Borrie, "Mitral Insufficiency: Experimental Circular Suture Around the Atrioventricular Ring" 1955 (pp. 687-697).

(56) References Cited

OTHER PUBLICATIONS

Braunberger et al., Very Long-Term Results (More Than 20 Years) of Valve Repair With Carpentier's Techniques in Nonrheumatic Mitral Valve Insufficiency, Downloaded from circ.ahajournals.org, Aug. 26, 2008, 1-8-1-11.
Bryan et al., Prospective randomized comparison of Carbo Medics and St. Jude Medical bileaflet mechanical heart valve prostheses: Ten-year follow-up, The Journal of Thoracic and Cardiovascular Surgery, Mar. 2007, 614-622.e2, vol. 133, No. 3.
Burkoff, MD., Ph.D, et al., "A randomized multicenter clinical study to evaluate the safety and efficacy of the TandemHeart percutaneous ventricular assist device versus conventional therapy with intraaortic balloon pumping for treatment of cardiogenic shock," The Cardiovascular Research Foundation, accepted May 2, 2006, 8 pages.
Byrne et al., Percutaneous Mitral Annular Reduction Provides Continued Benefit in an Ovine Model of Dilated Cardiomyopathy, Downloaded from circ.ahajournals.org, Aug. 26, 2008, 3088-92.
Canadian Office Action dated Sep. 12, issued in Canadian Patent Application No. 2,627,517, 2 pages.
Carlson et al., Lead Perforation: Incidence in Registries, Pace Industry Viewpoint, Jan. 2008, 13-15, vol. 31.
Carpentier et al., Reconstructive surgery of mitral valve incompetence Ten-year appraisal, The Journal of Thoracic and Cardiovascular Surgery, Mar. 1980, 338-348, vol. 79, No. 3.
Carter, et al. "Surgical Treatment of Mitral Insufficiency" 1953 (pp. 574-583).
Casselman et al., Mitral Valve Surgery Can Now Routinely Be Performed Endoscopically, Downloaded from eire. ahajournals.org, Aug. 26, 2008, 11-48-11-54.
Cauchemez et al., High-Flow Perfusion of Sheaths for Prevention of Thromboembolic Complications During Complex Catheter Ablation in the Left Atrium, Journal of Cardiovascular Electrophysiology, Mar. 2004, 276-283, vol. 15, No. 3.
Clinical Trials.gov, Comparing the Effectiveness of a Mitral Valve Repair Procedure in Combination With Coronary 3 Artery Bypass Grafting (CABG) Versus CABG Alone in People with Moderate Ischemic Mitral Regurgitation, http://clinicaltrials.gov/ct2/show/record/NCT00806988?term=mitral+repair&rank=7, Feb. 24, 2009, 1-3.
Clinical Trials.gov, Safety and Efficacy Study of the PTMA Device to Reduce Mitral Valve Regurgitation in Patients With Heart Failure (PTOLEMY2Canada), hllp:l/clinicaltrials.gov/ct2/show/study/NCT00815386?term=Viacor&rank=3, 1-3, Aug. 1-3, 25, 2008, pp. 1-4.
Clinical Trials.gov, Study of Safety and Efficacy of the Percutaneous Reduction of Mitral Valve Regurgitation in Heart Failure Patients (PTOLEMY-2), hllp:l/clinicaltrials.gov/ct2/show/NCT00787293?term=Viacor&rank=5, 1-2, Aug. 25, 2008, pp. 1-3.
ClinicaiTrials.gov, Aachen Safety and Efficacy of the Percutaneous Transvenous Mitral Annuloplasty Device to Reduce Mitral Regurgitation (PTOLEMY), http://clinicaltrials.gov/ct2/show/NCT00572091 ?term=mitral+regurgitation&rank=2, Aug. 25, 2008, 1-3.
ClinicalTrials.gov, Feasibility Study of a Percutaneous Mitral Valve Repair System., http://clinicaltrials.gov/ct2/show/NCT00209339?term=mitral+valve&rank=3, Aug. 25, 2008, 1-4.
ClinicalTrials.gov, Montreal Safety and Efficacy of the Percutaneous Transvenous Mitral Annuloplasty Device (PTOLEMY), http://clinicaltrials.gov/ct2/show/NCT00571610?term=mitral+regurgitation&rank=13, Aug. 25, 2008, 1-4.
ClinicalTrials.gov, Pivotal Study of a Percutaneous Mitral Valve Repair System, http://clinicaltrials.gov/ct2/show/NCT00209274?term=mitral+valve&rank=1, Aug. 25, 2008, 1-4.
ClinicalTrials.gov, RESTOR-MV: Randomized Evaluation of a Surgical Treatment for Off-Pump Repair of the Mitral Valve, http://clinicaltrials.gov/ct2/show/NCT00120276?term=myocor&rank=1, Aug. 25, 2008, 1-5.
ClinicalTrials.gov, Safety and Efficacy of the Percutaneous Transvenous Mitral Annuloplasty Device to Reduce Mitral Regurgitation (PTOLEMY), http://clinicaltrials.gov/ct2/show/NCT00568230?term=mitral+valve&rank=53, Aug. 25, 2008, 1-3.
ClinicalTrials.gov, VIVID-Valvular and Ventricular Improvement Via iCoapsys Delivery-Feasibility Study, http:// clinicaltrials.gov/ct2/show/NCT00512005?term=mitral+valve&rank=12, Aug. 25, 2008, 1-4.
Cohen, Trans-Septal Technique for Tandemheart Insertion, Lenox Hill Heart and Vascular Institute of New York, Barcelona May 22-May 25, 2007, 18 pages.
Corbisiero et al., Does Size Really Matter? A Comparison of the Riata Lead Family Based on Size and Its Relation to Performance, Pace, Jun. 2008, vol. 31, 722-726.
Crabtree et al., Recurrent Mitral Regurgitation and Risk Factors for Early and Late Mortality After Mitral Valve Repair for Functional Ischemic Mitral Regurgitation, The Society of Thoracic Surgeons , 2008, 1537-43, 85.
Criber et al., Early Experience With Percutaneous Transcatheter Implantation of Heart Valve Prosthesis for the Treatment of End-Stage Inoperable Patients With Calcific Aortic Stenosis, Journal of the American College of Cardiology, Feb. 18, 2004, 698-703, vol. 43, No. 4.
Criber et al., Treatment of Calcific Aortic Stenosis With the Percutaneous Heart Valve- Mid-Term Follow-Up From the Initial Feasibility Studies: The French Experience, Journal of the American College of Cardiology, Mar. 21, 2006, vol. 47, No. 6, 1241-1223.
Danik et al., Timing of delayed perforation with the St. Jude Riata lead: A single-center experience and a review of the literature, Heart Rhythm Society, Dec. 2008, vol. 5, No. 12, 1667-1672.
De Bonis et al., Similar long-term results of mitral valve repair for anterior compared with posterior leaflet prolapse, The Journal of Thoracic and Cardiovascular Surgery, Feb. 2006, 364-370, vol. 131, No. 2.
Deloche et al., Valve repair with Carpentier techniques the second decade, The Journal of Thoracic and Cardiovascular Surgery, Jun. 1990, 990-1002, vol. 99, No. 6.
Del Valle-Fernandez et al., Transcatheter heart valves for the treatment of aortic stenosis: state-of-the-art, Minerva Cardioangiologica, Oct. 2008, vol. 56, No. 5, 543-556.
De Simone et al., A clinical study of annular geometry and dynamics in patients with ischemic mitral regurgitation: new insights into asymmetrical ring annuloplasty, European Journal of Cardio-thoracic Surgery, 2006, 355-361, 29.
Detaint et al., Surgical Correction of Mitral Regurgitation in the Elderly—Outcomes and Recent Improvements, Downloaded from circ.ahajournals.org, Aug. 26, 2008, 265-272.
Douthiti, Cardiac Dimensions® Inc. Receives CE Mark for CARILLQWM Mitral Contour SystemTM, Cardiac Dimensions— News, htpp:l/www.cardiacdimensions.com/usa/press-release-2-4-09.html, downloaded Feb. 24, 2009, 1-2.
Dubreuil et al., Percutaneous Mitral Valve Annuloplasty for Ischemic Mitral Regurgitation: First in Man Experience With a Tempory Implant, Catheterization and Cardiovascular Interventions, 2007, 1053-61, 69.
Duffy et al., Feasibility and Short-Term Efficacy of Percutaneous Mitral Annular Reduction for the Therapy of Funcitonal Mitral Regurgitation in Patients With Heart Failure, Catheterization and Cardiovascular Interventions, 2006, 205-210, 68.
Dvorin, Endovalve Inc., Pioneering percutaneous mitral valve replacement., Start-Up Windhover's Review of Emerging Medical Ventures, Jun./Jul. 2006, vol. 11, No. 7, 1-2.
Eisenhauer et al., Closure of Prosthetic Paravalvular Mitral Regurgitation With the Gianturco-Grifka Vascular Occlusion Device, Catheterization and Cardiovascular Interventions, 2001, 5 pages,vol. 54.
El Tchaninoff, Clinical results of percutaneous aortic valve implantation, Euro PCR07, Cribier-Edwards, 30 pages.
Epstein et al., Gross and Microscopic Pathological Changes Associated With Nonthoracotomy Implantable Defibrillator Leads, Downloaded from circ.ahajournals.org, Jul. 23, 2008, 1517-24.

(56) References Cited

OTHER PUBLICATIONS

Epstein et al., Embolic Complications Associated With Radiofrequency Catheter Ablation, The American Journal of Cardiology, Mar. 15, 1996, 655-658, vol. 77.
European Examination Report dated Aug. 11, 2011 issued in European Patent No. 08 755 418.4, 3 pages.
European Examination Report dated Aug. 4, 2011 issued in European Patent No. 06 816 336.9, 3 pages.
European Search Report dated Jul. 12, 1984 cited in EP0125393.
European Intent to Grant dated Feb. 22, 2013 issued in Europe Patent Application No. 08 755 418.4, 7 pages.
European Search Report dated Mar. 6, 2013 issued in European Patent Application No. 10804952.9, 8 pages.
European Office Action dated Nov. 7, 2013 issued in European Patent Application No. 10 804 952.9 (5 pages.).
Evalve reports 1st MitraClip treatments in the Netherlands, Medical Device Daily, Feb. 19, 2009, vol. 13, No. 32, 2 pages.
Extended European search report dated Nov. 30, 2010 issued in European Patent Application No. 08850467.5, 6 pages.
Extended European search report dated Nov. 30, 2010 issued in European Patent Application No. 08755418.4, 7 pages.
Extended European search report dated Nov. 30, 2010 issued in European Patent Application No. 08849442.2, 6 pages.
Extended European Search Report dated Dec. 1, 2010 issued in European Patent Application No. 08755426.7, 6 pages.
Extended European Search Report dated Dec. 14, 2010 issued in European Patent Application No. 06816336.9, 7 pages.
Fagundes et al., Safety of Single Transseptal Puncture for Ablation of Atrial Fibrillation: Retrospective Study from a Large Cohort of Patients, Journal of Cardiovascular Electrophysiology, Dec. 2007, 1277-81, vol. 18, No. 12.
Feldman et al., Patient selection for percutaneous mitral valve repair: insight from early clinical trial applications, Nature Clinical Practice Cardiovascular Medicine, Feb. 2008, 84-90, vol. 5, No. 2.
Feldman et al., Percutaneous Mitral Valve Repair Using the Edge-to-Edge Technique—Six-Month Results of the EVEREST Phase I Clinical Trial, Journal of the American College of Cardiology, Dec. 6, 2005, 2134-40, vol. 46, No. 11.
Fernandez et al., Early and late-phase events after valve replacement with the St. Jude Medical prosthesis in 1200 patients, The Journal of Thoracic and Cardiovascular Surgery, Feb. 1994, 394-407, vol. 107, No. 2.
Fitts et al., Fluoroscopy-Guided Femoral Artery Puncture Reduces the Risk of PCI-Related Vascular Complications, Journal of Interventional Cardiology, vol. 21, No. 3, 2008, 273-278.
French catheter scale chart http://en.wikipedia.org/wiki/French_catheter_scale_chart, Dec. 20, 2006, 1 page.
Fukuda et al., Maintenance of Geometric Alterations Associated with Percutaneous Mitral Valve Repair: Real-Time Three-Dimensional Echocardiographic Assessment in an Ovine Model, J. Heart Valve Dis, May 2008, vol. 17, No. 3, 276-282.
Gelsomino et al., Left ventricular diastolic function after restrictive mitral ring annuloplasty in chronic ischemic mitral regurgitation and its predictive value on outcome and recurrence of regurgitation, International Journal of Cardiology, vol. 132,2009,419-428.
General Physical Properties of PVA Sponge (values are not guaranteed), Ceiba Technologies, http://www.ceibatech.com/PVASpongeDate.htm, Dec. 20, 2006 3 pages.
Geyfman et al.. Cardiac Tamponade as Complication of Active-Fixation Atrial Lead Perforations: Proposed Mechanism and Management Algorithm. PACE, Apr. 2007, vol. 30, 498-501.
Gillinov et al., Durability of Mitral Valve Repair for Degenerative Disease, The Journal of Thoracic and Cardiovascular Surgery, Nov. 1998, 734-743, vol. 116, No. 5.
Glenn, et al., "The Surgical Treatment of Mitral Insufficiency with Particular Reference to the Application of a Vertically Suspended Graft" Jul. 1956 (pp. 59-77).
Glenn, et al., "The Implantation of a Vascularized Graft in the Chambers of the Heart" 1954 (pp. 5-11 ).
Glenn, et al., "The Surgical Treatment of Mitral Insufficiency: the Fate of a Vascularized Transchamber Intracardiac Graft" Apr. 1955 (pp. 510-518).
Glover, et al., "The Fate of Intracardiac Pericardia! Grafts as Applied to the Closure of Septal Defects and to the Relief of Mitral Insufficiency" 1952 (pp. 178-185).
Gorman et al., Surgical Therapy for Mitral Regurgitation: The Key to Preventing Heart Failure?, Prevention of Hean Failure After Myocardial Infarction, 2008, 211-215.
Grossi et al., Intraoperative Effects of the Coapsys Annuloplasty System in a Randomized Evaluation (RESTOR-MV) of Functional Ischemic Mitral Regurgitation, The Society of Thoracic Surgeons, 2005, 1706-11, 80.
Grossi et al., Late Results of Mitral Valve Reconstruction in the Elderly, The Society of Thoracic Surgeons, 2000, 1224-6,70.
Grossi et al., Minimally Invasive Mitral Valve Surgery: A 6-Year Experience With 714 Patients, The Society of Thoracic Surgeons, 2002, 660-4, 74.
Harken, et al., "The Surgical Treatment of Mitral Insufficiency," The Journal of Thoracic Surgery,1954 (pp. 604-627).
Harken, et al., "The Surgical Correction of Mitral Insufficiency" 1953 (pp. 4-7).
Harper, Evalve Announces Enrollment Completion of the Everest Randomized Study, http://www.evalveinc.com/ europe/press/17.html, downloaded Feb. 24, 2009, 1-3.
Harper, Two-Year Follow-Up Data Demonstrates Preservation of Adequate Mitral Valve Area in Patients Treated with the MitraCiip®-system, http://www.evalveinc.com/europe/press/21.html, downloaded Feb. 24, 2009, 1-3.
Henderson, et al., "The Surgical Treatment of Mitral Insufficiency" Jun. 1953 (pp. 858-868).
Hendren et al., Mitral Valve Repair for Ischemic Mitral Insufficiency, The Society of Thoracic Surgeons, 1991, 1246-52, 52.
Heupler et al., Infection Prevention Guidelines for Cardiac Catheterization Laboratories, Catheterization and Cardiovascular Diagnosis, 1992, 260-263, 25.
Hourihan et al., Transcatheter Umbrella Closure of Valvular and Paravalvular Leaks, American College of Cardiology, Nov. 15, 1992,7 pages, vol. 20, No. 6.
Hung et al., 3D Echocardiography: A Review of the Current Status and Future Directions, Ase Position Paper, Journal of the American Society of Echocardiography, Mar. 2007, 213-233.
Hung et al., Mechanism of Dynamic Regurgitant Orifice Area Variation of Functional Mitral Regurgitation-Physiologic Insights From the Proximal Flow Convergence Technique, Journal of the American College of Cardiology, Feb. 1999, vol. 33, No. 2, 538-545.
Hung et al., A Novel Approach for Reducing Ischemic Mitral Regurgitation by Injection of a Polymer of Reverse Remodel and Reposition Displaced Papillary Muscles, Circulation—Journal of the American Heart Association, Sep. 30, 2008, Downloaded from circ.ahajournals.org at National Insthealth Lib on Feb. 25, 2009, S262-S269.
Hvass et al., Papillary Muscle Sling: A New Functional Approach to Mitral Repair in Patients With Ischemic Left Ventricular Dysfunction and Functional Mitral Regurgitation, The Society of Thoracic Surgeons, 2003, 809-11, 75.
Hytowitz, First U.S. Patients Enrolled in the Realism Continued Access Study, evalve, http://www.evalveinc.com/ europe/press/22/ html, downloaded Feb. 24, 2009, 2 pages.
Ibrahim et al., the St. Jude Medical prosthesis—A thirteen-year experience, The Journal of Thoracic and Cardiovascular Surgery, Aug. 1994, 221-230, vol. 108, No. 2.
Intent to Grant dated Jan. 2, 2013 issue in European Patent Application No. 06816336.9, 7 pages.
International Search Report and Written Opinion dated Sep. 22, 2008 issued in PCT Application No. PCT/US08/63560 11 pages.
International Search Report and Written Opinion dated Sep. 29, 2008 issued in PCT Application No. PCT/US08/63568 12 pages.
International Preliminary Report on Patentability dated Jan. 31, 2012 issued in PCT Patent Application No. PCT/ US2010/043360, 7 pages.

(56) References Cited

OTHER PUBLICATIONS

International Search Report and Written Opinion dated Feb. 25, 2009 issued in PCT Application No. PCT/ US08/083570, 13 pages.
International Search Report and Written Opinion dated Apr. 2, 2009 issued in PCT Application No. PCT/US08/083574, 8 pages.
International Search Report and Written Opinion dated Jul. 6, 2010 issued in PCT Patent Application No. PCT/US2010/032764, 9 pages.
International Search Report and Written Opinion dated Sep. 22, 2008 issued in PCT Application No. PCT/ US08/63568. 11 pages.
International Search Report and Written Opinion dated Sep. 29, 2008 issued in PCT Application No. PCT/ US08/63568. 12 pages.
International Search Report and Written Opinion, dated May 11, 2007 (6 pages) filed in corresponding PCT application PCT/US06/39011 (8 pages).
International Search Report and Written Opinion dated Jan. 16, 2009 issued in PCT Application No. PCT/US08/83497 10 pages.
International Search Report and Written Opinion dated Sep. 21, 2010 issued in PCT Patent Application No. PCT/US201 0/043360, 9 pages.
International Search Report and Written Opinion dated Aug. 11, 2009 issued in PCT Application No. PCT/ US2009/046995, 11 pages.
International Preliminary Report on Patentability dated May 27, 2010 issued in PCT/US2008/083574, 4 pages.
International Preliminary Report on Patentability and Written Opinion, issued in PCT/US2008/063560, dated Nov. 26, 2009, 8 pages.
International Preliminary Report and Written Opnion issued in PCT/US2008/083570, dated May 27, 2010, 4 pages.
Iskandar et al., Tricuspid Valve Malfunction and Ventricular Pacemaker Lead: Case Report and Review of the Literature, Echocardiography: A Jrnl of CV Ultrasound & Allied Tech., 2006, 692-697, vol. 23, No. 8.
Jilaihawi et al., Percutaneous Aortic Valve Replacement in Patients with Challenging Aortoiliofemoral Access, Catheterization and Cardiovascular Interventions, 2008, vol. 72, 885-890.
Johns, et al., "Mitral Insufficiency: the Experimental Use of a Mobile Polyvinyl Sponge Prosthesis," Annals of Surgery, Sep. 1954 (pp. 335-341).
Jovin et al.. Atrial Fibrillation and Mitral Valve Repair, Pace, Aug. 2008, vol. 31, 1057-1063.
Kahlert et al., Direct Assessment of Size and Shape of Noncircular Vena Contracta Area in Functional Versus Organic Mitral Regurgitation Using Real-Time Three-Dimensional Echocardiography, Valvular Heart Disease, Journof the American Society of Echocardiography, Aug. 2008, vol. 21, No. 8, 912-921.
Kasegawa et al., Mitral Valve Repair for Anterior Leaflet Prolapse With Expanded Polytetraftuoroethylene Sutures, The Society of Thoracic Surgeons, 2006, 1625-31, 81.
Kaye et al., Feasibility and Short-Term Efficacy of Percutaneous Mitral Annular Reduction for the Therapy of Heart Failure-Induced Mitral Regurgitation, Downloaded from circ.ahajournals.org, Aug. 26, 2008, 1795-97.
Kempfert et al., Minimally invasive off-pump valve-in-a-valve implantation: the atrial transcatheter approach for re-operative mitral valve replacement, European Heart Journal, 2008, vol. 29, 2382-2387.
Kerensky, Complications of Cardiac Catheterization and Strategies to Reduce Risks, Diagnostic and Therapeutic Cardiac Catheterization, 1998, Chapter 8, 91-105.
Kodali et al., Transcatheter Valve Repair and Replacement, Downloaded from arjournals.annualreviews.org by National Institute of Health Library on Feb. 25, 2009, 14 pages.
Koertke et al., INR Self-Management Permits Lower Anticoagulation Levels After Mechanical Heart Valve Replacement, downloaded from circ.ahajournals.org, Aug. 26, 2008, 11-75-11-78.
Kratz et al., St. Jude Prosthesis for Aortic and Mitral Valve Replacement: A Ten-Year Experience, The Society of Thoracic Surgeons, 1993, 462-8, 56.
Kron et al., Surgical Relocation of the Posterior Papillary Muscle in Chronic Ischemic Mitral Regurgitation, The Society of Thoracic Surgeons, 2002,600-1,74.
Kuck et al., Best of Structural Heart Disease Abstracts, TCT-124, The American Journal of Cardiology, Oct. 20-25, 2007, 58L.
Kuwahara et al., Mechanism of Recurreni/Persistent Ischemic/Functional Mitral Regurgitation in the Chronic Phase After Surgical Annuloplasty—Importance of Augmented Posterior Leaftet Tethering, Circulation, Jul. 4, 2006, 1-529-1-534.
Kwan et al., Geometric Differences of the Mitral Apparatus Between Ischemic and Dilated Cardiomyopathy With Significant Mitral Regurgitation—Real-Time Three-Dimensional Echocardiography Study, Circulation, Mar. 4, 2003, 1135-1140.
Laskey et al., Multivariable Model for Prediction of Risk of Significant Complication During Diagnostic Cardiac Catheterization, Catheterization and Cardiovascular Diagnosis, 1993, 185-190, 30.
Lee et al., Mitral Valve Reconstruction: Experience Related to Early and Late Mortality and Reoperation, J Heart Valve Dis, Nov. 2005,715-721, vol. 14, No. 6.
Leung et al., Percutaneous Mitral Valve Repair—An overview of the current devices and techniques, Coronary/ Cardiac Interventions—Endovascular Today, Oct. 2006, 26-33.
Levine et al., Mechanistic Insights into Functional Mitral Regurgitation, Valvular Heart Disease, 2009, 125-129.
Liddicoat et al., Percutaneous Mitral Valve Repair: A Feasibility Study in an Ovine Model of Acute Ischemic Mitral Regurgitation, Catheterization and Cardiovascular Interventions, 2003, 410-416, 60.
Lim et al., Percutaneous Transthoracic Ventricular Puncture for Diagnostic and Interventional Catheterization, Catheterization and Cardiovascular Interventions, 2008, 915-918, 71.
Lin et al., Severe Symptomatic Tricuspid Valve Regurgitation Due to Permanent Pacemaker or Implantable Cardioverter-Defibrillator Leads, Journal of the American College of Cardiology, May 17, 2005, 1672-5, vol. 45, No. 10.
Little et al., Three-Dimensional Ultrasound Imaging Model of Mitral Valve Regurgitation: Design and Evaluation, Ultrasound in Medicine and Biology, 2008, vol. 34, No. 4, 647-654.
Llaneras et al., Large Animal Model of Ischemic Mitral Regurgitation, The Society of Thoracic Surgeons—Ischemic Mitral Insufficiency, 1994, vol. 57, 432-439.
Lozonschi et al., Transapical Mitral Valved Stent Implantation, The Society of Thoracic Surgeons, 2008, 745-8, 86.
Mack, Percutaneous Therapies for Mitral Regurgitation: Where Do We Stand and Where Are We Going? Do Current Devices Really Represent a Step Forward Compared to Surgery?, 2007 Heart Valve Summit, Jun. 7, 2007, 59 pages.
Magne et al., Ischemic Mitral Regurgitation: A Complex Multifaceted Disease, Cardiology, 2009, vol. 112, 244-259.
Maleki et al., Intracardiac Ultrasound Detection of Thrombus on Transseptal Sheath: Incidence, Treatment, and Prevention, Journal of Cardiovascular Electrophysiology, Jun. 2005, 561-565, vol. 16, No. 6.
Maniu et al., Acute and Chronic Reduction of Functional Mitral Regurgitation in Experimental Heart Failure by Percutaneous Mitral Annuloplasty, Journal of the American College of Cardiology, Oct. 19, 2004, 1652-61, vol. 44, No. 8.
Matthews, Anatomy of the Heart, Definitions Cardiology Explained and Presented by Robert Matthews, MD, http:!/ www.rjmatthewsmd.com/Definitions/anatomy_oflhe_heart.htm, printed Jul. 28, 2008, 265 pages.
McClure et al.. Early and late outcomes in minimally invasive mitral valve repair: An eleven-year experience in 707 patients, Acquired Cardiovascular Disease, The Journal of Thoracic and Cardiovascular Surgery, Jan. 2009, vol. 137, No. 1, 70-75.
McGee et al., Recurrent mitral regurgitation after annuloplasty for functional ischemic mitral regurgitation, Surgery for Acquired Cardiovascular Disease, The Journal of Thoracic and Cardiovascular Surgery, Dec. 2004, 916-924.e4, vol. 128, No. 6.
Mehra et al., Surgery for Severe Mitral Regurgitation and Left Ventricular Failure: What Do We Really Know?, Journal of Cardiac Failure, Mar. 2008, 145-150. vol. 14, No. 2.

(56) References Cited

OTHER PUBLICATIONS

Menicanti et al., Functional Ischemic Mitral Regurgitation in Anterior Ventricular Remodeling: Results of Surgical Ventricular Restoration with and Without Mitral Repair, Heart Failure Reviews, 2004, 317-327, 9.
Messas et al., Efficacy of Chordal Cutting to Relieve Chronic Persistent Ischemic Mitral Regurgitation, Circulation, Sep. 9, 2003, 11-111-11-115.
Meurin et al., Thromboembolic events early after mitral valve repair: Incidence and predictive factors, International Journal of Cardiology, 2008, 45-52, 126.
Mirable et al., What are the characteristics of patients with severe, symptomatic, mitral regurgitation who are denied surgery?, The European Society of Cardiology, 2007, 1358-65,28.
Mitchell et al., Complications, Cardiac catheterization and coronary intervention, Chapter 9, 2008, 238-270.
Mishra et al., Coapsys Mitral Annuloplasty for Chronic Functional Ischemic Mitral Regurgitation: 1-Year Results, The Society of Thoracic Surgeons, 2006, 42-46, 81.
Modi et al., Minimally invasive mitral valve surgery: a systematic review and meta-analysis, European Journal of Cardia-Thoracic Surgery, 2008, vol. 34, 943-952.
Moore, et al., "Unsuitability of Transventricular Autogenous Slings for Diminishing Valvular Insufficiency" Feb. 1953 (pp. 173-182).
Morgan et al.. Left Heart Catheterization by Direct Ventricular Puncture: Withstanding the Test of Time, Catheterization and Cardiovascular Diagnosis, 1989, 87-90, 16.
Moscucci et al., Coil Embolization of a Periprosthetic Mitral Valve Leak Associated With Severe Hemolytic Anemia, Images in Cardiovascular Medicine, American Heart Association, Inc., 2001, 2 pages, vol. 104.
Mullins, Flow directed catheters ("floating" balloon catheters), Cardiac Catheterization in Congenital Heart Disease; Pediatric and Adult, 2006, Chapter 7, pp. 213-221, 9 pages, Blackwell Futura, USA.
Mullins. Vascular access. Cardiac Catheterization in Congenital Heart Disease; Pediatric and Adult, 2006, Chapter 4, pp. 115-117, 5 pages, Blackwell Futura, USA.
Mullins, Aortic valve dilation, Cardiac Catheterization in Congenital Heart Disease; Pediatric and Adult, 2006, Chapter 19, pp. 487-489, 5 pages, Blackwell Futura, USA.
Mullins, Foreign body removal, Cardiac Catheterization in Congenital Heart Disease; Pediatric and Adult, 2006, Chapter 12, pp. 350-377, 30 pages, Blackwell Futura, USA.
Murday et al., A Prospective Controlled Trial of St. Jude Versus Starr Edwards Aortic and Mitral Valve Prostheses, The Society of Thoracic Surgeons, 2003, 66-74, 76.
Myers, Jr., et al., Color Doppler Velocity Accuracy Proximal to Regurgitant Orifices: Influence of Orifice Aspect Ratio, Ultrasound in Medicine and Biology, 1999, vol. 25, No. 5, 771-792.
Nifong et al., Robotic mitral valve surgery: A United States multicenter trial, The Journal of Thoracic and Cardiovascular Surgery, Jun. 2005, 1395-1404, vol. 129, No. 6.
Ning et al., Live three-dimensional transesophageal echocardiography in mitral valve surgery, Chinese Medical Journal, 2008, vol. 121, No. 20,2037-2041.
Noto et al., Cardiac Catheterization 1990: A Report of the Registry of the Society for Cardiac Angiography and Interventions (SCA&I), Catheterization and Cardiovascular Diagnosis, 1991, 75-83, 24.
Notzold et al., Microemboli in aortic valve replacement, Future Drugs Ltd, Expert Rev. Cardiovasc. Ther., Vo14, No. 6, 2006, 853-859.
Ohlow et al., Incidence and outcome of femoral vascular complications among 18,165 patients undergoing cardiac catheterisation, International Journal of Cardiology, 2008, 1-6.
Onundarson et al., Warfarin anticoagulation intensity in specialist-based and in computer-assisted dosing practice, International Journal of Laboratory Hematology, 2008, vol. 30, 382-389.
Otsuji et al., Insights From Three-Dimensional Echocardiography Into the Mechanism of Functional Mitral Regurgitation—Direct In Vivo Demonstration of Altered Leaflet Tethering Geometry, Circulation, Sep. 16, 1997, vol. 96, No. 6, 1999-2008.
Pai et al., Effect of Atrial Fibrillation on the Dynamics of Mitral Annular Area, J. Heart Valve Dis., Jan. 2003, vol. 12, No. 1, 31-37.
Palacios et al., Safety and Feasibility of Acute Percutaneous Septal Sinus Shortening: First-In-Human Experience, Catheterization and Cardiovascular Interventions, 2007, vol. 69, 513-518.
Paniagua et al., First Human Case of Retrograde Transcatheter Implantation of an Aortic Valve Prosthesis, Texas Heart Institute Journal, Transcatheter Aortic Valve Prosthesis, 2005, vol. 32, No. 3, 393-398.
Pedersen et al., iCoapsys Mitral Valve Repair System: Percutaneous Implantation in an Animal Model, Catheterization and Cardiovascular Interventions, 2008, 125-131,72.
Piazza et al., Transcatheter Mitral Valve Repair for Functional Mitral Regurgitation: Coronary Sinus Approach, Journal of Interventional Cardiology, 2007, 495-508, vol. 20, No. 6.
Preliminary Report on Patentability dated Nov. 10, 2011 issued in PCT Patent Application No. PCT/ US2010/032764, 4 pages.
Prifti et al., Ischemic Mitral Valve Regurgitation Grade II-III: Correction in Patients with Impaired Left Ventricular Function undergoing Simultaneous Coronary Revascularization, J Heart Valve Dis, Nov. 2001, 754-762, vol. 10, No. 6.
PVA Datasheet, www.sponge-pva.com/data.htm. Dec. 20. 2006, 2 pages.
PVA Sponge W (wet) & D (dry), Ceiba Technologies, http://www.ceibatech.com/PVASpongeW&D.htm, Dec. 20, 2007 5 pages.
Rashkind et al. Nonsurgical closure of patent ductus arteriosus: clinical application of the Rash kind PDA Occluder System, Therapy and Prevention—Congenital Heart Disease, Mar. 1987, 10 pages, vol. 75, No. 3.
Richardson et al., Is a port-access mitral valve repair superior to the sternotomy approach in accelerating postoperative recovery?, Interactive CardioVascular and Thoracic Surgery, Downloaded from icvts.ctsnetjournals.org, Aug. 26, 2008, 670-683, 7.
Rinaldi et al., Best of Structural Heart Disease Abstracts, TCT-123, The American Journal of Cardiology, Oct. 20-25, 2007, 57L.
Rodes-Cabau et al., Feasibility and Initial Results of Percutaneous Aortic Valve Implantation Including Selection of the Transfemoral or Transapical Approach in Patients With Severe Aortic Stenosis, The American Journal of Cardiology, 2008, 1240-1246.
Ruiz, New Percutaneous Approaches for Mitral Regurgitation, Lenox Hill Heart and Vascular Institute of New York, May 13-16, 2008, 26 pages.
Rumel et al., Section on Cardiovascular Diseases—The Correction of Mitral Insufficiency With a Trans-Valvular Polyvinyl Formalinized Plastic (Ivalon) Sponge Prosthesis, American College of Chest Physicians, Apr. 1958, Downloaded from chestjournal.org, Jul. 23, 2008, 401-413.
Ryhanen et al, "In vivo biocompatibility evaluation of nickel-titanium shape memory metal alloy: Muscle and perineural tissue responses and encapsule membrane thickness," Jan. 19, 1998, Journal of Biomedical Materials Research, 41, 481.
Sakakibara, "A Surgical Approach to the Correction of Mitral Insufficiency" Aug. 1955 (pp. 196-203).
Satpathy et al., Delayed Defibrillator Lead Perforation: An Increasing Phenomenon, Pace, Jan. 2008, vol. 31, 10-12.
Schofer, Percutaneous MVR: Clinical Evaluation—The Carillon Experience, EuroPCR 2007, Barcelona, Spain, Ma~22-25, 2007, 35 pages.
Schwammenthal et al., Dynamics of Mitral Regurgitant Flow and Orifice Area—Physiologic Application of the Proximal Flow Convergence Method: Clinical Data and Experimental Testing, Circulation, Jul. 1994, vol. 90, No. 1, 307-322.
Seeburger et al., Minimal invasive mitral valve repair for mitral regurgitation: results of 1339 consecutive patients, European Journal of Cardio-thoracic Surgery, 2008, 1-6.
Siminiak et al., Best of Structural Heart Disease Abstracts, TCT-125, The American Journal of Cardiology, Oct. 20-25, 2007, 58L.
Southard et al., Current Catheter-Based Treatments of Functional Mitral Regurgitation, Cardiac Interventions Today, Jun. 2007,41-44.

(56) References Cited

OTHER PUBLICATIONS

Spencer, Viacor, Inc. Announces First Patient Treated in PTOLEMY-2 Study, http://www.viacorinc.com/viacor_news.html, Nov. 14, 2008, downloaded Feb. 24, 2009, 2 pages.
Sterlinski et al., Subacute cardiac perforations associated with active fixation leads, Clinical Research Leads and Lead Extraction, Europace, 2009, vol. 11, 206-212.
Svensson et al., United States Feasibility Study ofTranscatheter Insertion of a Stented Aortic Valve by the Left Ventricular Apex, The Society of Thoracic Surgeons, 2008, 46-55, 86.
SPI-Chem™ Vinylec® (Formvar®) Resins, http://www.2spi.com/catalog/submal/formvar-resins.shtml, Dec. 20, 2006, 5 pages.
Toledano et al., Mitral regurgitation: Determinants for referral for cardiac surgery by Canadian cardiologists, Can J. Cardiol, Mar. 1, 2007, 209-214, vol. 23, No. 3.
Tops et al., Percutaneous Valve Procedures: An Update, Curr Probl Cardiol, Aug. 2008, 417-426.
Trippel, et al., "Reinforced Ivalon Sponge as an Aortic Prosthesis" Feb. 1960 (9 pages).
Turakhia et al., Rates and severity of perforation from implantable cardioverter-defibrillator leads: A 4-year study, J Intery Card Electrophysiol, 2009, vol. 24, 47-52.
Vahanian, The Cardiologist's Perspective on the Future of Percutaneous Mitral Valve Repair, Euro PCR07, 53 pages.
Vahanian, Coronary Sinus and Direct Annuloplasty Percutaneous Mitral Valve Repair, Innovations in Cardiovascular Interventions, Dec. 7-9, 2008, Tel-Aviv, Israel, 22 pages.
Vahanian, Edwards MONARC system—Evolution Interim Results, 31 pages.
Vahanian, Overview on Percutaneous Mitral Valve Technology, Euro PCR07, Transcatheter Valve Symposium, Barcelona, May 22-25, 2007, 23 pages.
Van Gelder et al., Diagnosis and Management of Inadvertently Placed Pacing and ICD Leads in the Left Ventricle: A Multicenter Experience and Review of the Literature, Pace, May 2000, vol. 23, 877-883.
Vinylec® Resins, http://www.2spi.com/catalog/submal/vinylec-physical.html, Dec. 20, 2006, 1 page.
Vranckx et al., The Tandem Heart®, percutaneous transseptalleft ventricular assist device: a safeguard in high-risk percutaneous coronary interventions. The six-year Rotterdam experience, Clinical research EuroInterv., 2008, vol. 4, 331-337.
Walther et al., Transapical minimally invasive aortic valve implantation; the initial 50 patients, European Journal o Cardio-thoracic Surgery, 2008, 983-988, 33.
Webb et al., Percutaneous Mitral Annuloplasty With the MONARC System: Preliminary Results From the Evolution Trial, TCT-103, The American Journal of Cardiology, Oct. 22-27, 2006, 49M.
Webb et al., Percutaneous Transvenous Mitral Annuloplasty—Initial Human Experience with Device Implantation in the Coronary Sinus, downloaded from circ.ahajournals.org, Aug. 26, 2008, 851-855.
Webster et al., Impact of transvenous ventricular pacing leads on tricuspid regurgitation in pediatric and congenital heart disease patients, J Interv Card Electrophysiol, 2008, 65-68, 21.
Wolf et al., Solid and gaseous cerebral micorembolization after biologic and mechanical aortic valve replacement: Investigation with multirange and multifrequency transcranial Doppler ultrasound, The Journal of Thoracic and Cardiovascular Surgery, Mar. 2008, vol. 135, No. 3, 512-520.
Xiangming et al., In Vivo Characterization of Attachment Safety Between Cardiac Pacing Lead and Canine Heart Muscle*, Acta Mechanica Salida Sinica, Sep. 2007, vol. 20, No. 3, 189-197.
Yamaura et al., Geometrical Demonstration and Three-Dimensional Quantitative Analysis of the Mitral Valve With Real-Time Three-Dimensional Echocardiography: Novel Anatomical Image Creation System, J Echocardiogr, 2004, vol. 2, No. 4, 99-104.
Ye et al., Six-month outcome of transapical transcatheter aortic valve implantation in the initial seven patients, European Journal of Cardio-thoracic Surgery, 2007, 16-21, 31.
Yosefy et al., Proximal Flow Convergence Region as Assessed by Real-time 3-Dimensional Echocardiography: Challenging the Hemispheric Assumption, Journal of the American Society of Echocardiography, Apr. 2007, vol., No. 4, 389-396.
Yoshida, et al., Assessment of Left-to-Right Atrial Shunting After Percutaneous Mitral Valvuloplasty by Transesophageal Color Doppler Flow-Mapping, Circulation, Dec. 1989, 1521-1526, vol. 80, No. 6.
Zhou et al., Thromboembolic Complications of Cardiac Radiofrequency Catheter Ablation: A Review of the Reported Incidence. Pathogenesis and Current Research Directions. Journal of Cardiovascular Electrophysiology, Apr. 1999, 611-620, vol. 10, No. 4.
Office Action received in Chinese Application No. 201480028456.7, dated Oct. 18, 2016; 12 pages.
Office Action received in Chinese Application No. 201480045369.2, dated Sep. 1, 2016; 12 pages.
Office Action received in Chinese Application No. 201480028344.1, dated Nov. 15, 2016; 10 pages.
Extended European Search Report dated Oct. 7, 2016 issued in European Patent Application No. 14769641.3; 8 pages.
Extended European Search Report dated Oct. 10, 2016 issued in European Application No. 14770314.4; 8 pages.

SECTION B-B

TRANS-APICAL IMPLANT SYSTEMS, IMPLANTS AND METHODS

CROSS-REFERENCE AND RELATED APPLICATIONS

The present application is a continuation of U.S. patent application Ser. No. 13/838,752, filed Mar. 15, 2013, which is incorporated herein by reference in its entirety.

FIELD

The present disclosure relates to the repair and/or correction of dysfunctional heart valves, and more particularly pertains to heart valve implants and systems and methods for delivery and implementation of the same.

BACKGROUND

A human heart has four chambers, the left and right atrium and the left and right ventricles. The chambers of the heart alternately expand and contract to pump blood through the vessels of the body. The cycle of the heart includes the simultaneous contraction of the left and right atria, passing blood from the atria to the left and right ventricles. The left and right ventricles then simultaneously contract forcing blood from the heart and through the vessels of the body. In addition to the four chambers, the heart also includes a check valve at the upstream end of each chamber to ensure that blood flows in the correct direction through the body as the heart chambers expand and contract. These valves may become damaged, or otherwise fail to function properly, resulting in their inability to properly close when the downstream chamber contracts. Failure of the valves to properly close may allow blood to flow backward through the valve resulting in decreased blood flow and lower blood pressure.

Mitral regurgitation is a common variety of heart valve dysfunction or insufficiency. Mitral regurgitation occurs when the mitral valve separating the left coronary atrium and the left ventricle fails to properly close. As a result, upon contraction of the left ventricle blood may leak or flow from the left ventricle back into the left atrium, rather than being forced through the aorta. Any disorder that weakens or damages the mitral valve can prevent it from closing properly, thereby causing leakage or regurgitation. Mitral regurgitation is considered to be chronic when the condition persists rather than occurring for only a short period of time.

Regardless of the cause, mitral regurgitation may result in a decrease in blood flow through the body (cardiac output). Correction of mitral regurgitation typically requires surgical intervention. Surgical valve repair or replacement is carried out as an open heart procedure. The repair or replacement surgery may last in the range of about three to five hours, and is carried out with the patient under general anesthesia. The nature of the surgical procedure requires the patient to be placed on a heart-lung machine. Because of the severity/complexity/danger associated with open heart surgical procedures, corrective surgery for mitral regurgitation is typically not recommended until the patient's ejection fraction drops below 60% and/or the left ventricle is larger than 45 mm at rest.

In some instances, patients who are suffering from mitral regurgitation are also in need of an aortic valve replacement. Studies have shown, for example, that about 30% of patients who are in need of an aortic valve replacement also have moderate to sever mitral regurgitation. Typically, these patients only receive an aortic valve replacement, and the mitral regurgitation is not treated. One method of aortic valve replacement includes trans-apical aortic valve. A trans-apical aortic valve replacement may be delivered via a trans-apical approach which utilizes a short incision (e.g., 3-4 inch long) between two ribs to gain access to the apex of the left ventricle. This is sometimes referred to as a "mini-thoracotomy," and is much less invasive than the traditional method of getting access to the heart; a median sternotomy which involves cracking the sternal bone in the middle and spreading the chest wide open.

Another common heart condition includes coronary artery disease which may be treated by coronary artery bypass graft (CABG) surgery via a mini-thorcotomy. Sometimes such patients can also benefit from concomitant mitral repair. In fact, sometimes the patient has mitral regurgitation because of the coronary blockage, and CABG alone is not enough to treat the mitral regurgitation.

Accordingly, there exists a need to treat mitral regurgitation, particularly using a trans-apical approach.

BRIEF DESCRIPTION OF THE DRAWINGS

Features and advantage of the claimed subject matter will be apparent from the following description of embodiments consistent therewith, which description should be considered in conjunction with the accompanying drawings, wherein:

DESCRIPTION

Figure 1:
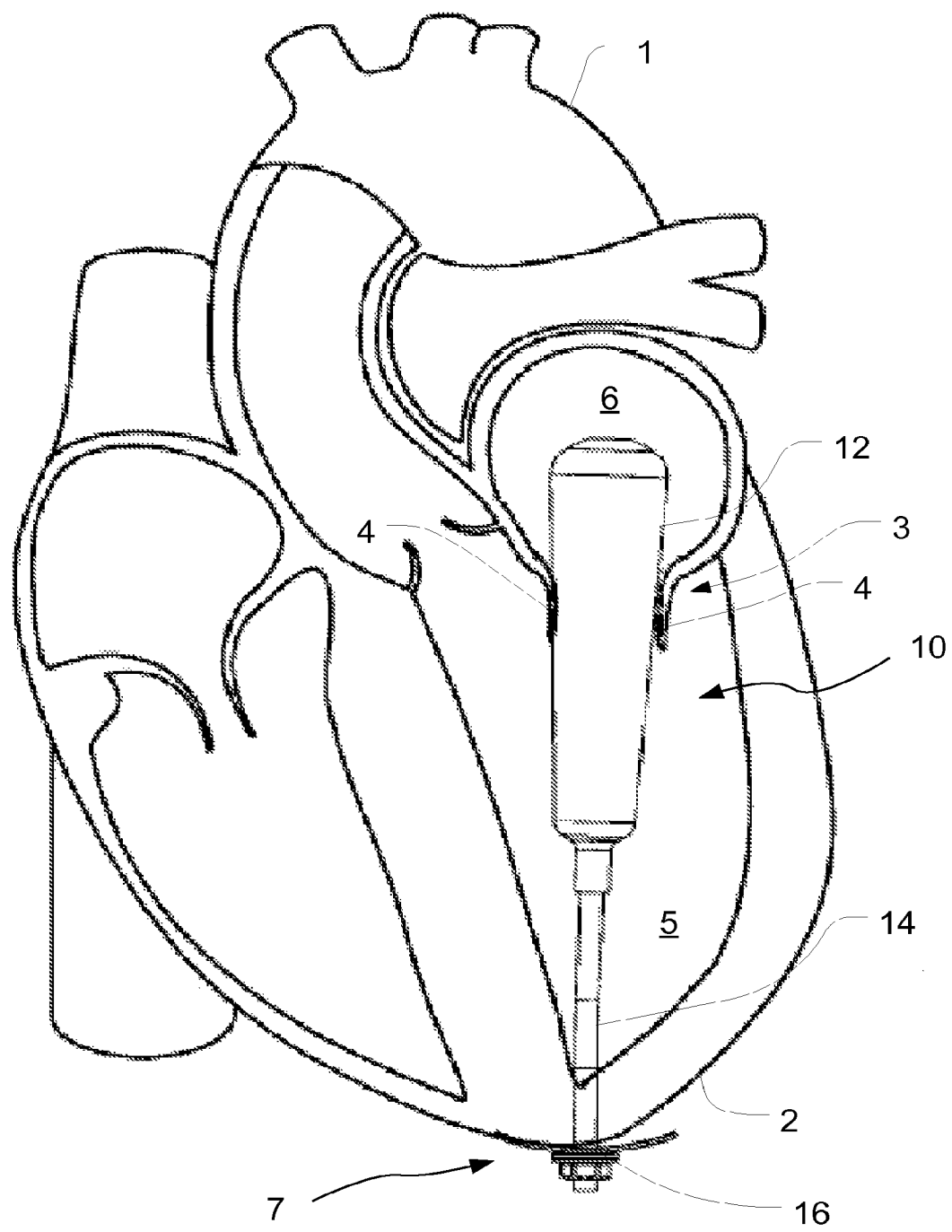
FIG. 1 is a perspective view of one embodiment of a mitral valve implant consistent with the present disclosure.

By way of an overview, a perspective view of one embodiment of a trans-apical mitral valve implant 10 is illustrated within the heart 1 is generally illustrated in FIG. 1. The trans-apical mitral valve implant 10 (hereinafter referred to simply as the implant 10 and/or mitral valve implant 10) includes a spacer 12, a shaft 14, and optionally an anchor assembly 16. In general, the mitral valve implant 10 is delivered within the heart 1 and anchored to the native coronary tissue 2 as generally illustrated in FIG. 1 such that at least a portion of the spacer 12 is disposed proximate a mitral valve 3 and the mitral valve implant 10 may interact and/or cooperate with at least a portion of the native mitral valve 3 to reduce and/or eliminate excessive regurgitation. For example, at least a portion of one or more cusps 4 of the heart 1 valve may interact with, engage, and/or seal against at least a portion of the heart valve implant 10 (for example, but not limited to, the spacer 12) when the mitral valve 3 is in a closed condition. The interaction, engagement and/or sealing between at least a portion of at least one cusp 4 and at least a portion of the heart valve implant 10 may reduce and/or eliminate regurgitation in a heart valve 3, for example, providing insufficient sealing, including only a single cusp 4, e.g., following removal of a diseased and/or damaged cusp 4, and/or having a ruptured cordae. A heart valve implant 10 consistent with the present disclosure may be used in connection with various additional and/or alternative defects and/or deficiencies.

As discussed in greater detail herein, the mitral valve implant 10 is delivered to the mitral valve 3 within the left ventricle 5 and/or left atrium 6 by way of a trans-apical approach. A short incision (e.g., 3-4 inch long) between two ribs is formed to gain access to the apex 8 of the left ventricle 5. An incision is made through the apex 8 to gain access to the left ventricle 5. The mitral valve implant 10 is then introduced into the mitral valve 3, the spacer 12 is expanded, and the anchor is secured to the native coronary tissue 2 of the heart 1, for example, on the outside of the heart 1 proximate to the apex 7.

The mitral valve implant 10 provides numerous benefits. For example, the mitral valve implant 10 may be installed to reduce/prevent mitral regurgitation on a beating heart (i.e., without removing the patient's heart and without cardiopulmonary bypass (CPB) surgery). The trans-apical approach is therefore less invasive compared to a median sternotomy. Additionally, as noted above, many patients who suffer from mitral regurgitation also suffer from other conditions which necessitate trans-apical surgery. As such, the mitral valve implant 10 according to the present invention allows for the treatment of mitral regurgitation without requiring significant invasive surgery (e.g., the mitral valve implant 10 may be implanted while the patient is already undergoing trans-apical surgery to address other medical conditions).

Figure 2:
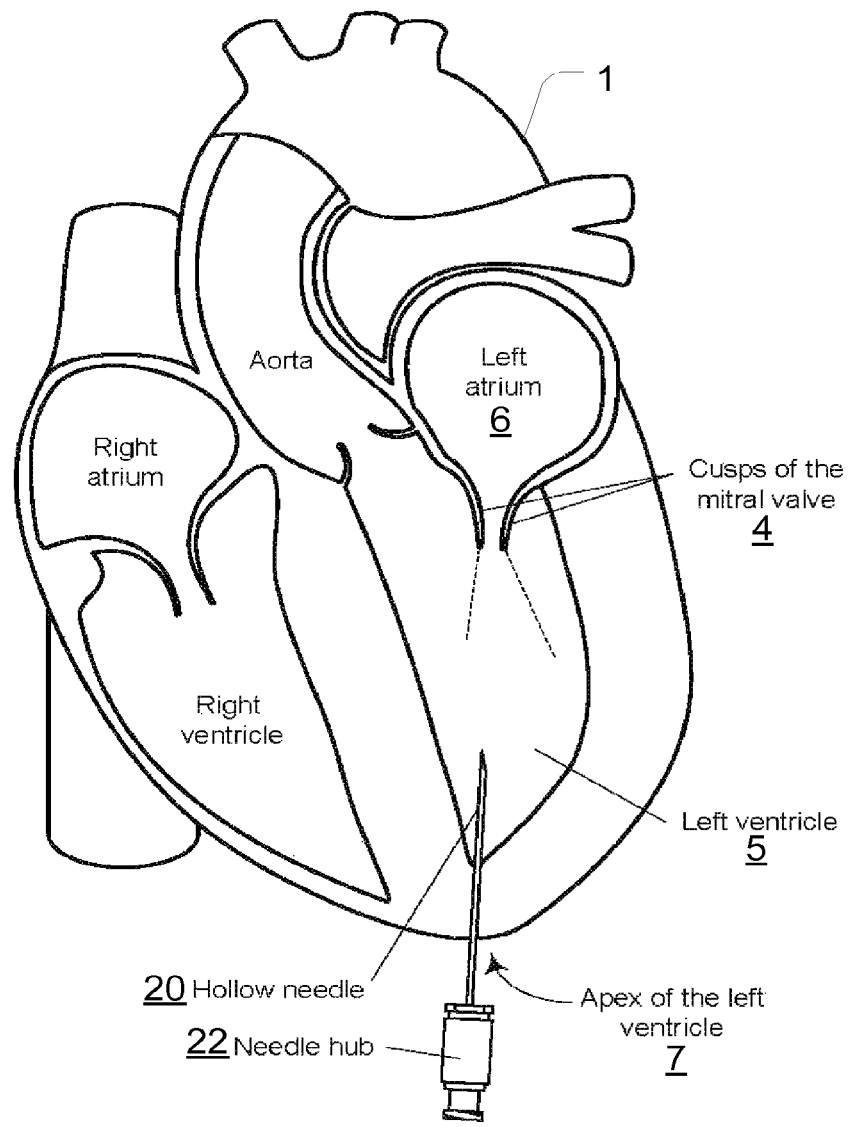
FIG. 2 generally illustrates a needle being inserted through the apex into the left ventricle.
Figure 3:
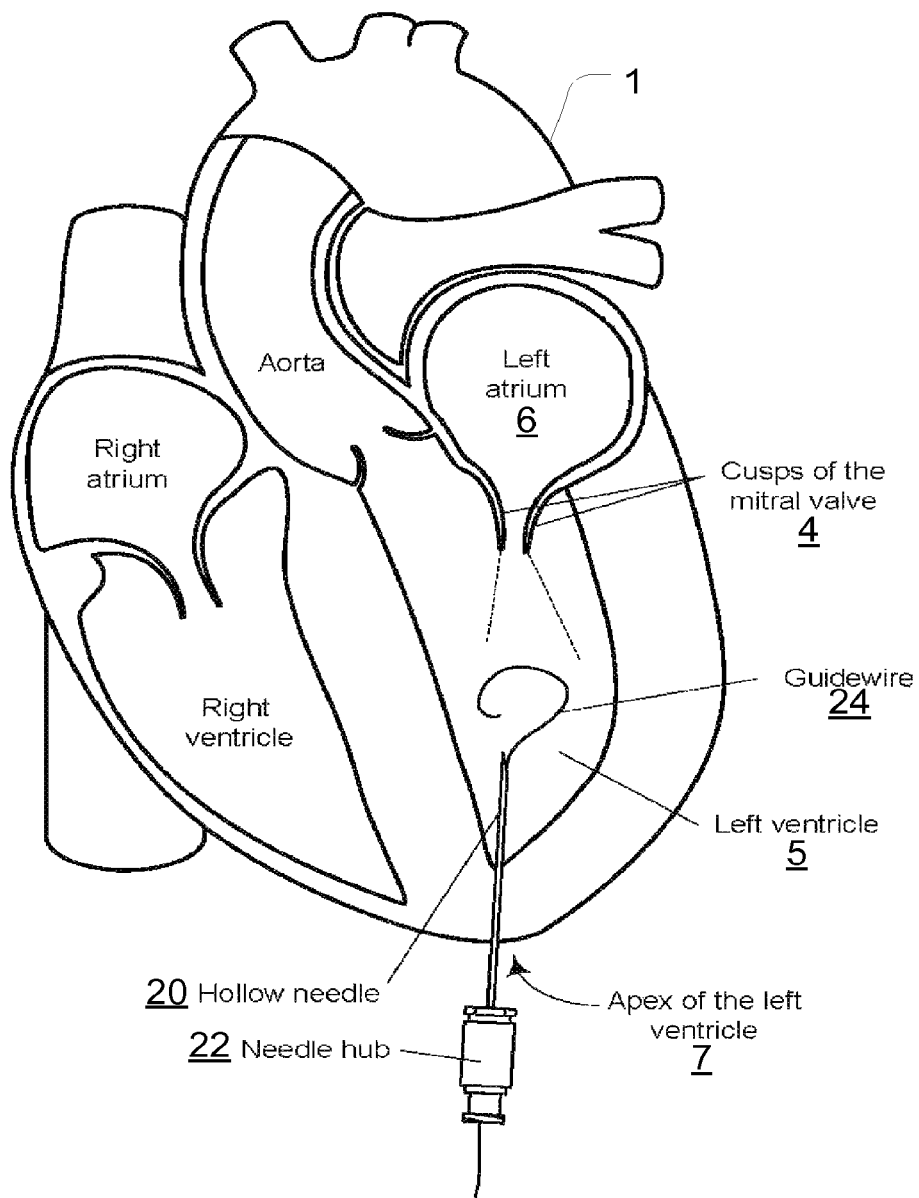
FIG. 3 generally illustrates a guidewire being inserted through the needle into the left ventricle.

With reference to FIG. 2, the trans-apical system and method includes gaining access to the left ventricle 5. For example, a hollow needle 20 (which may be coupled to a needle hub 22) is inserted through the apex 7 of the left ventricle 5 and into the left ventricle 5. Once access has been achieved to the left ventricle 5, a guide wire 24 is introduced through the lumen of the hollow needle 20 into the left ventricle 5 as generally illustrated in FIG. 3. The guide wire 24 may include a ⅟₃₂" wire and may optionally form a curved, pig-tail-like shape after the guide wire 24 exits the lumen of the hollow needle 20 in the left ventricle 5.

Figure 4:
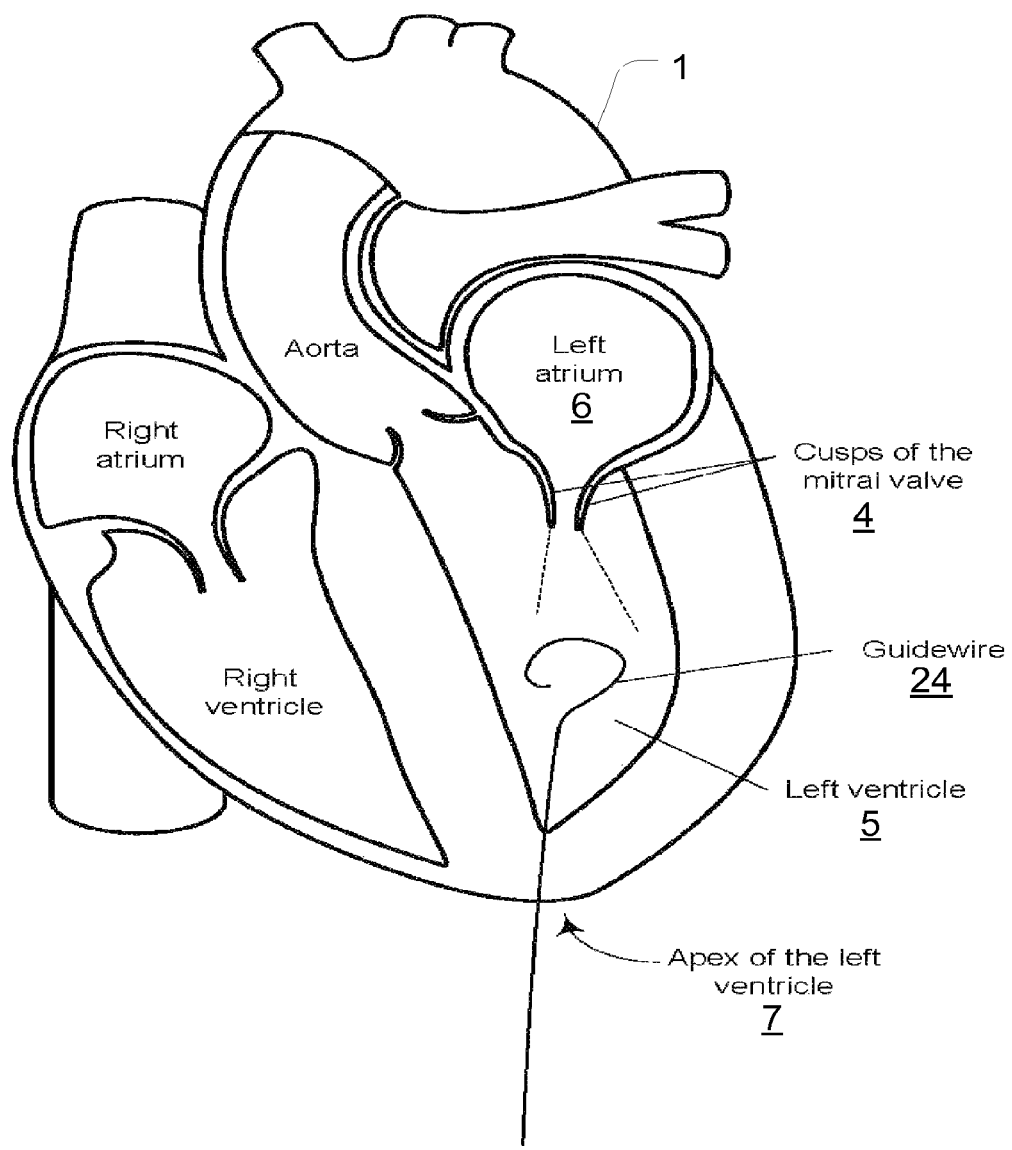
FIG. 4 generally illustrates the needle removed and the guidewire in the left ventricle.
Figure 5:
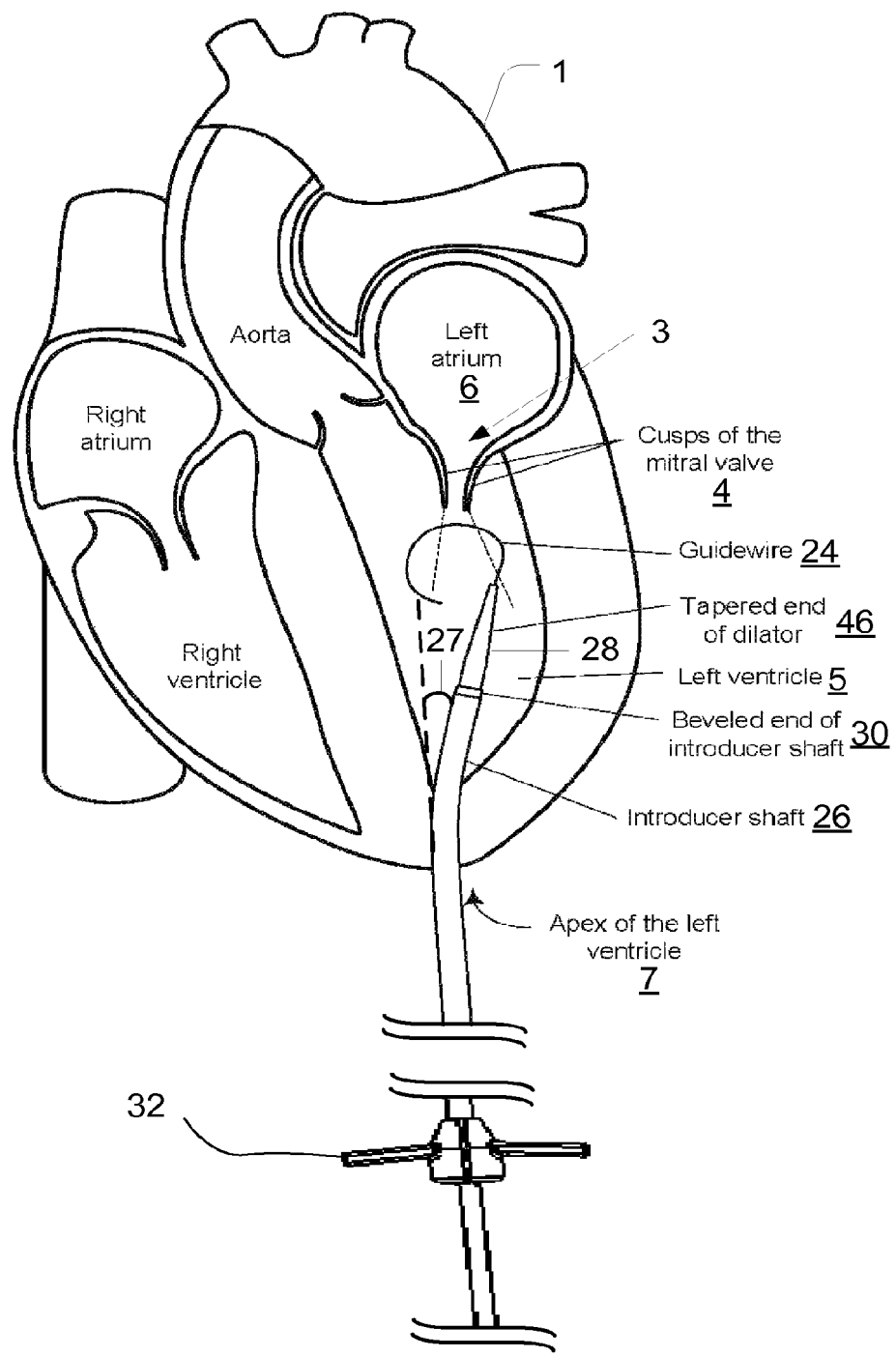
FIG. 5 generally illustrates one embodiment of an introducer and dilator being inserted into the left ventricle.

With the guide wire 24 in the left ventricle 5, the hollow needle 20 is removed from heart 1, leaving the guide wire 24 remaining in the left ventricle 5 as generally illustrated in FIG. 4. The guide wire 24 may be used as a pathway for advancing other instruments and devices into the heart 1. For example, an introducer 26 and/or dilator 28 may be advanced along the guide wire 24 into the left ventricle 5 as generally illustrated in FIG. 5.

The distal end 30 of the shaft of the introducer 26 may be beveled to aid in passing the introducer 26 through incision in the apex 7. The introducer 26 may also feature a predefined bend 27. The predefined bend 27 is formed in the introducer 26 during the manufacturing of the introducer 26 and is configured to facilitate alignment of the distal end 30 of the introducer 26 with the mitral valve 3. Without the bend 27 (e.g., if the introducer was just linear), it would be very difficult to align the tip 30 of the introducer 26 with the mitral valve 3 and between the two papillary muscles, and into the outflow tract of the mitral valve 3. While the bend/curvature 27 does not appear to be perfectly aligned with the mitral valve 3, this is due (in part) to the three-dimensional path which is not readily shown in a two-dimensional drawings. The bend 27 may be disposed at an angle of approximately 20-40 degrees, for example 30 degrees, from the longitudinal axis of the main portion of the introducer 26 extending outwardly from the incision in the apex 7.

The introducer 26 may optionally include a splitter (also referred to as the introducer hub) 32 configured to longitudinally split the shaft of the introducer 26 such that the introducer 26 forms a split catheter which can be easily removed while allowing an object within the lumen of the introducer 26 (e.g., the guidewire 24 and/or a portion of the implant 10) to remain within the lumen of the introducer 26. The splitter 32 may include a seal configured to allow another device and/or lumen to be selectively and removably sealed and/or advanced through the to the splitter 32 into the lumen of the introducer 26.

For example, the splitter 32 (introducer hub) may include at least two parts, namely, an outer shell made of a polymer that has been molded in such a way as to provide a preferential and controlled break-away seam, and the inner seal made of silicone rubber also with a molded break-away seam. The outer shell and silicone seal are mechanically connected so that the break-away seams are both positioned along the same axis as the shaft/lumen of the introducer 26. The splitter 32 (introducer hub) is mechanically connected to the proximal end of the introducer's tubular shaft. When the "handles" of the outer shell of the splitter 32 (introducer hub) are actuated in opposite directions, with sufficient force, rotating away from the axis of the introducer 26 toward the distal end of the introducer 26, the preferential break-away seams of the outer shell and of the inner seal of the splitter 32 (introducer hub) permanently separate and propagate a tear in the wall of the tube of the introducer 26. Continuing to further separate the handles of the splitter 32 (introducer hub) in turn continues to advance the tear in the tube of the introducer 26. The user continues to separate the handles, tearing the tube until the tear reached the distal end of the tube and completes the axial separation of the introducer 26.

Figure 6:
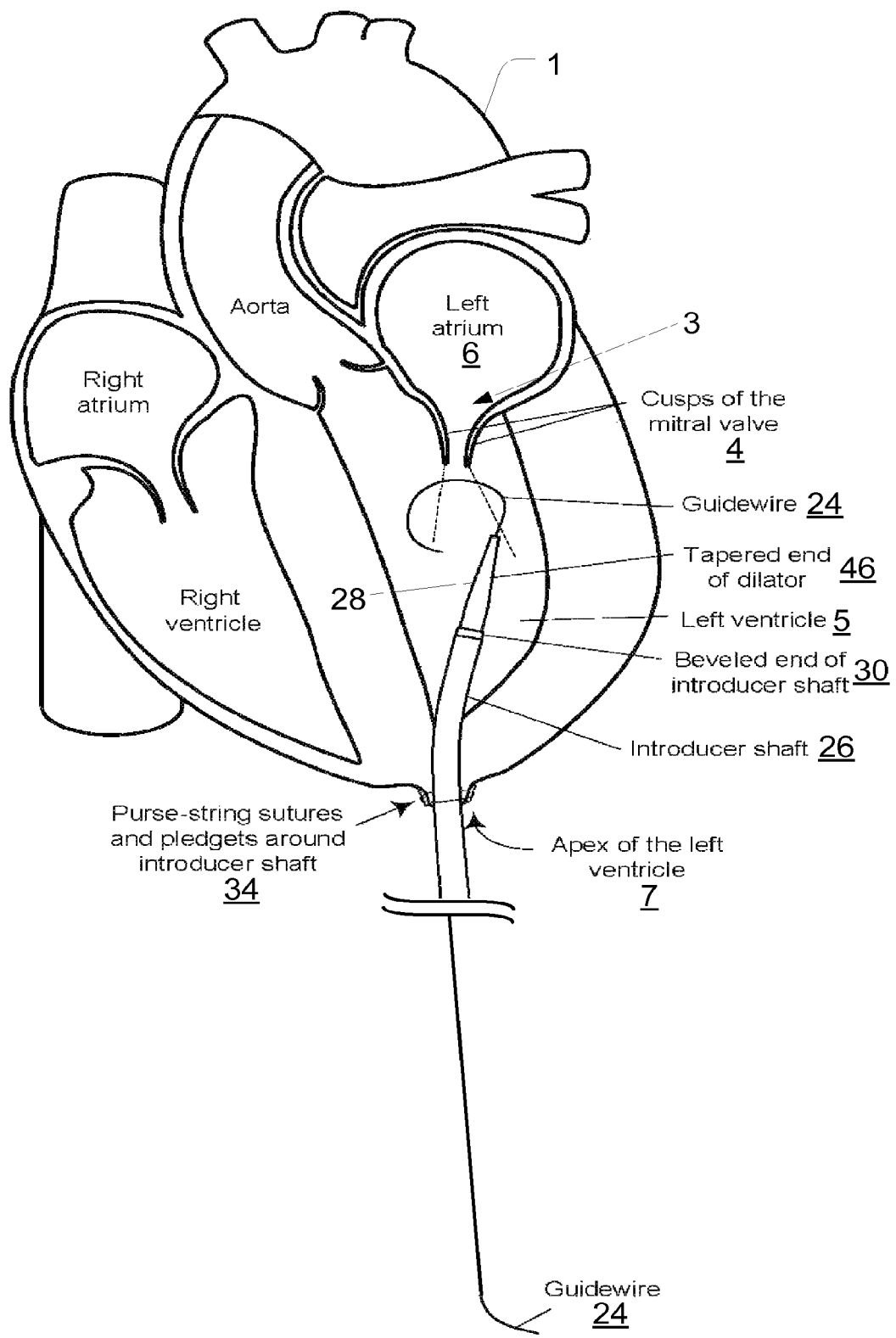
FIG. 6 generally illustrates purse-string sutures and pledgets secured around the introducer.

Once the introducer 26 has been advanced into the left ventricle 5 through the incision in the apex 7, one or more purse-string sutures and/or pledgets 34 may be secured around the shaft of the introducer 26 and the incision as generally illustrated in FIG. 6. The purse-string sutures and/or pledgets 34 are configured to apply a radially compressive force against the shaft of the introducer 26 during the procedures, thereby minimizing the potential for accidentally tearing the heart tissue proximate to the incision and also minimizing blood loss during the procedure. For example, one or more heavy-gauge sutures may be passed around the shaft of the introducer 26 in a continuous loop, so that when it is all the way around, the suture can be pulled tight like a noose or purse-string to hold the surrounding tissue tightly around the introducer 26. To prevent the suture from tearing through the tissue, each time the suture passes through tissue, the suture also passes through a small pledget of woven polyester fabric. Optionally, two purse-strings (each with four pledgets) may be used to secure the introducer 26 to the left ventricle wall.

One embodiment of a dilator 28 may include define at least one lumen configured to receive at least a portion of the delivery guide wire 24. For example, the lumen may have an internal diameter of approximately 0.038". The dilator 28 may also comprise a shaft including a tapered tip region 46. The tapered distal tip 46 may be provided to facilitate advancing the tip 46 into the puncture site in the apex 7 as the dilator 28 is introduced over the delivery guide wire 24. The shaft may comprise a plurality of segments or portions having different stiffness or hardness to produce the desired overall curvature. The shaft may be formed from one or more suitable polymers such as, but not limited to, a polyether block amide. The shaft may have a constant inner and/or outer diameter and may be made from different materials to provide the various stiffness or hardness. Alternatively, or in addition, the shaft may have different inner and/or outer diameters and may be made from one or more materials. For example, the various stiffness or hardness of the shaft may be provided by varying the thickness of the shaft at the different segments or portions. The different hardness of the segments may provide differing degrees of bending stiffness to the dilator 28 which may facilitate advancing the dilator 28 into and/or out of the left ventricle 3.

Figure 7:
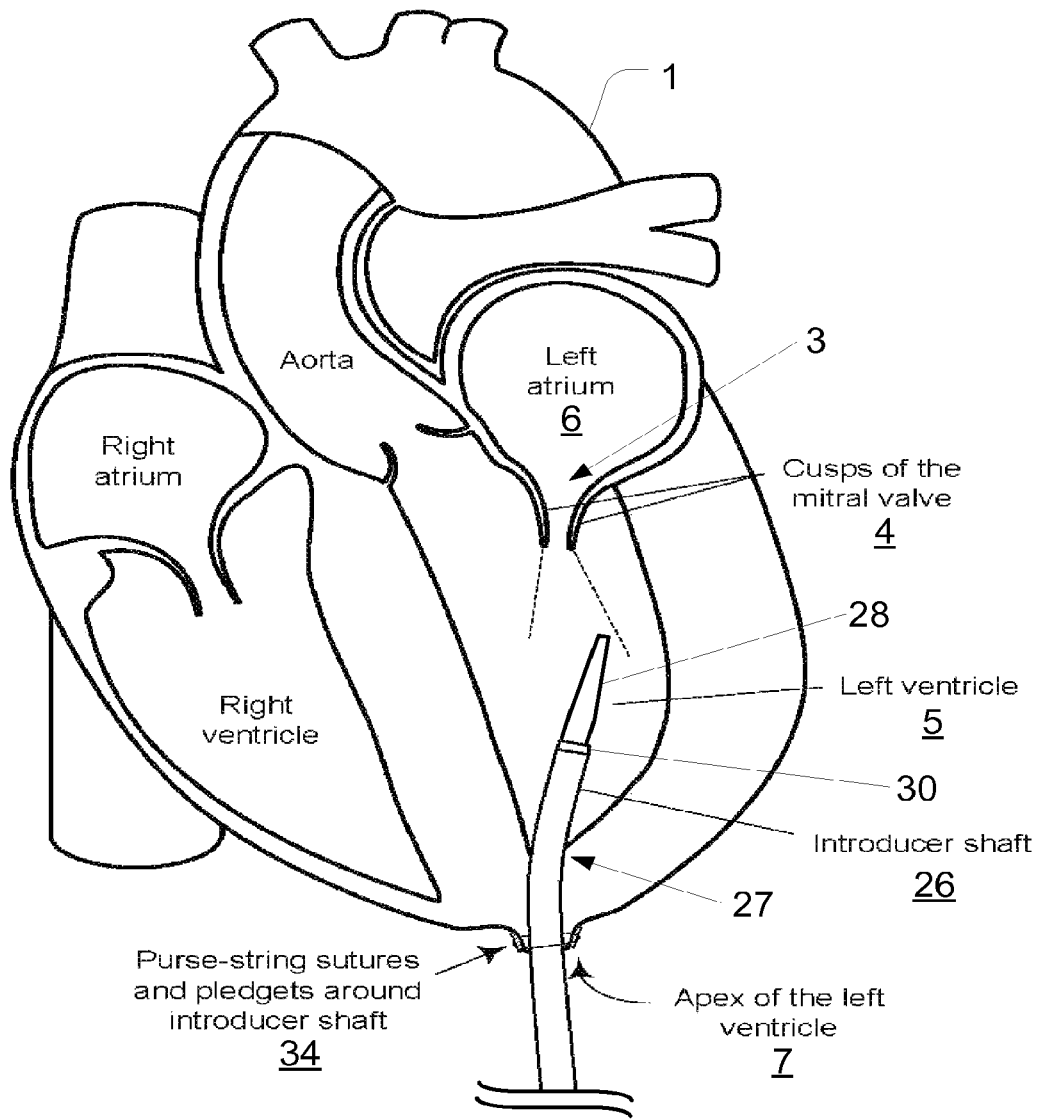
FIG. 7 generally illustrates the guidewire removed from the introducer.
Figure 8:
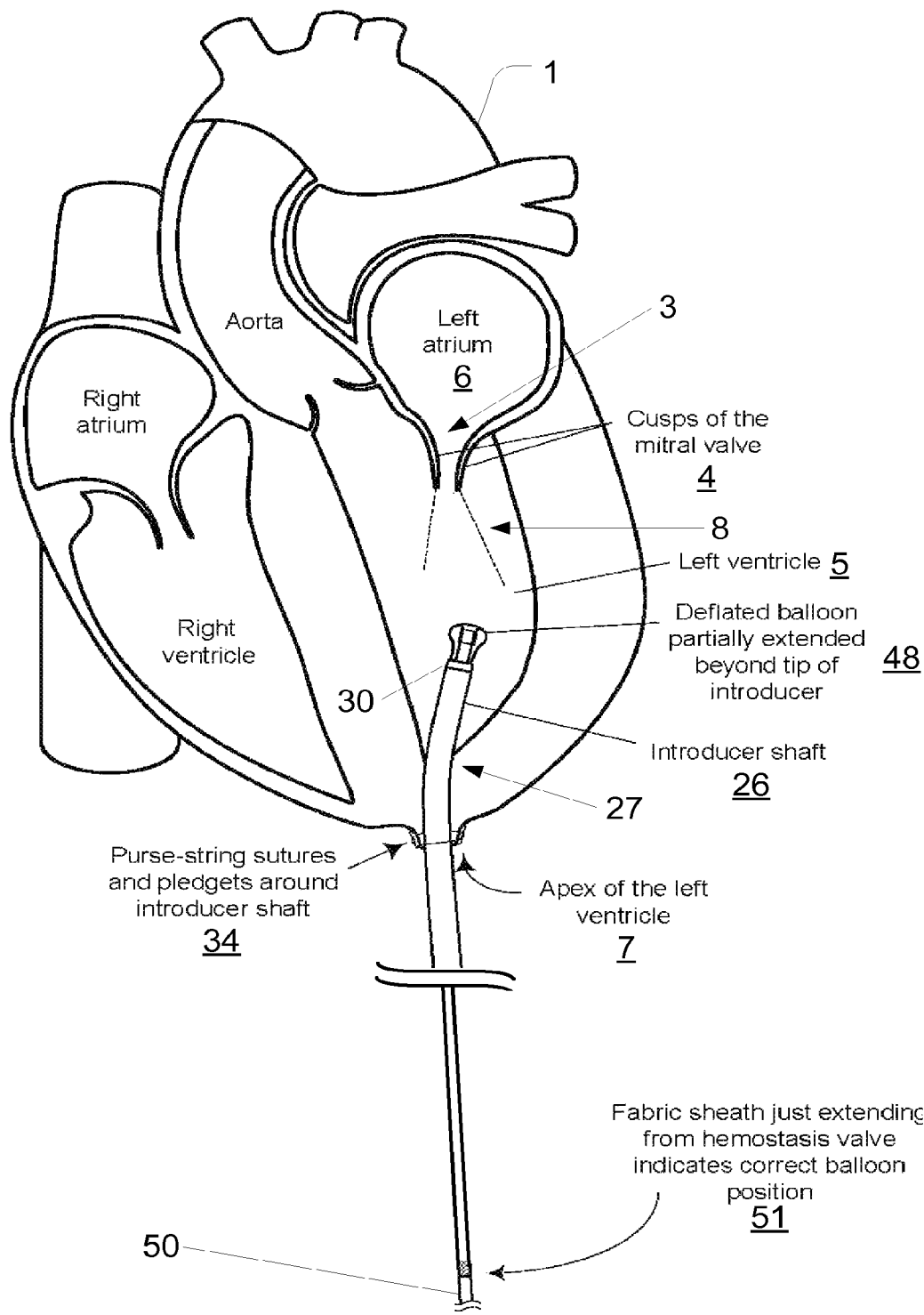
FIG. 8 generally illustrates one embodiment of a messenger balloon partially beyond the tip of the introducer.

Once the introducer 26 is positioned in the left ventricle 5, the guidewire 24 may be removed, leaving the introducer 26 and dilator 28 in the left ventricle 5 as generally illustrated in FIG. 7. Because of the predetermined bend 27, the distal end 30 of the introducer 26 and/or dilator 28 is generally aligned with the mitral valve 3. A deflated messenger balloon 48 may be advanced through the lumen of the introducer 26 and/or dilator 28 until at least a portion of the deflated messenger balloon 48 exits the distal end 30 of the introducer 26 and/or dilator 28 as generally illustrated in FIG. 8 (the dilator 28 is shown retracted into the introducer 26 for clarity). A shaft 50 of the messenger balloon 48 may include indicia 51 for indicating the position of the messenger balloon 48 relative to the introducer 26. For example, when the indicia (which may include the proximal end of a fabric covering the shaft 50) is aligned with and/or protrudes a few millimeters from the splitter 32, about 1 cm of the messenger balloon 48 is protruding from the end 30 of the introducer 26.

Figure 9:
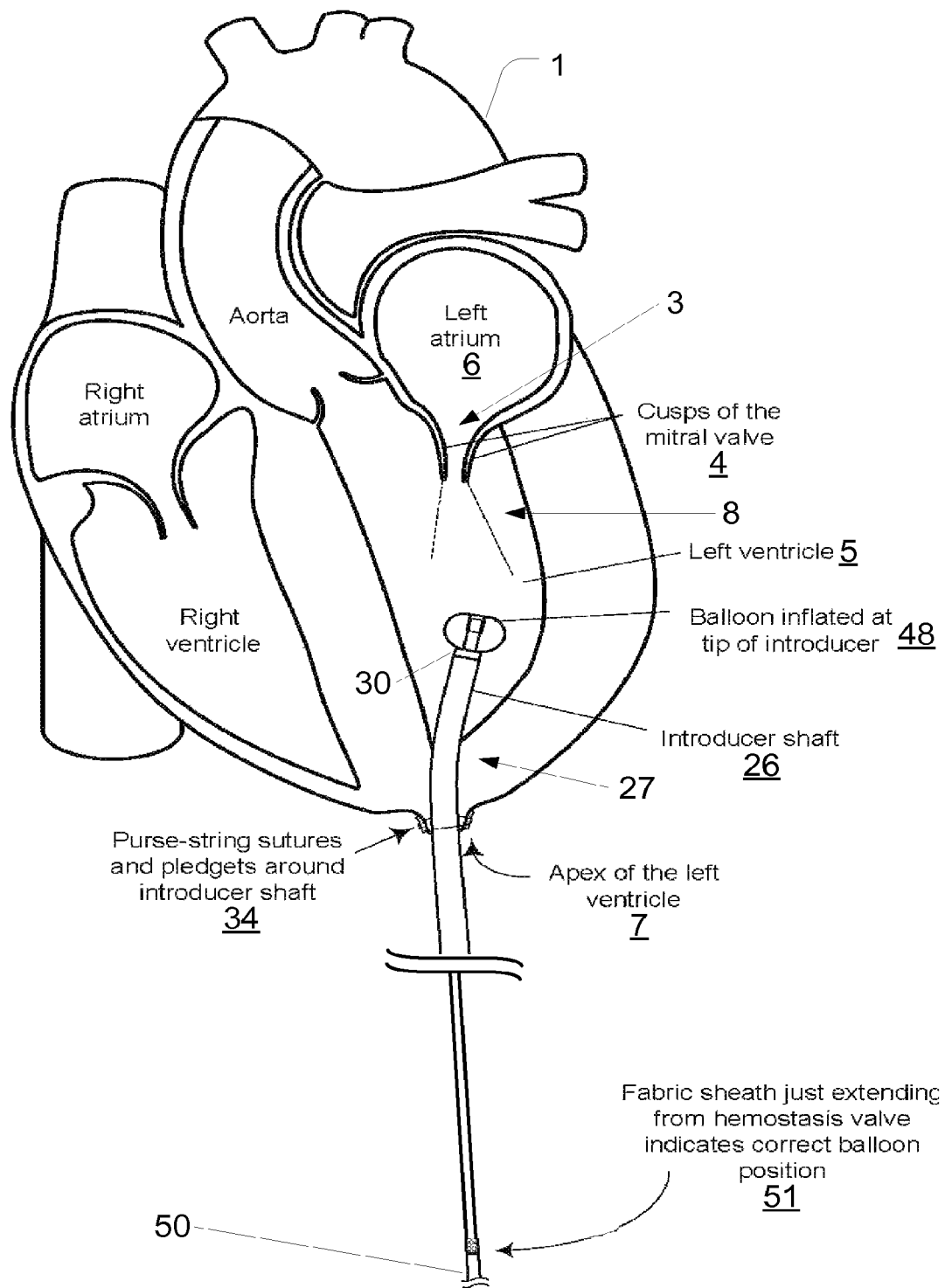
FIG. 9 generally illustrates the messenger balloon inflated at the tip of the introducer.

The messenger balloon 48, when expanded, is configured to facilitate advancement of the introducer 26 and/or dilator 28 through the mitral valve 3 without damaging the mitral valve 3 or becoming entangled in the mitral valve 3 (for example, the cusps 4, the chordae and/or papillary muscles 8 of the mitral valve 3). The messenger balloon 48 may be disposed proximate the distal end region of a shaft 50 and may be fluidly coupled through the shaft 50 to an expansion medium such as, but not limited to, a gas and/or liquid which may expand and/or enlarge the messenger balloon 48 from the deflated or retracted position as generally illustrated in FIG. 8 to the inflated or expanded position as generally illustrated in FIG. 9 (note, that the messenger balloon 48 is only partially extending from the introducer 26). The messenger balloon 48 forms a soft tip which serves as an atraumtic "bumper" tip to minimize the risk of damaging or even irritating the delicate lining (endocardium) of the left ventricle 5. To much contact with the left ventricle 5 can cause a dangerous arrhythmia. According to at least one embodiment, the expansion medium may include carbon dioxide $CO_2$ gas and/or saline. Optionally, contrast media may be introduced into the messenger balloon 48 to allow the messenger balloon 48 to be more easily visually located using fluoroscopy or the like. The contrast media may coat the inside surface of the messenger balloon 48.

The messenger balloon 48 may include a resiliently expandable/collapsible material such as, but not limited to, silicone, Yulex™ or the like which may be selectively collapsed and/or expanded. The messenger balloon 48 may be bonded to the shaft 50 and may include one or more passageways, apertures or lumens to allow the expansion medium to expand/collapse the messenger balloon 48. The diameter of the messenger balloon 48 should be small enough in the first or retracted/collapsed position to be advanced over the delivery guide wire 24 through the introducer 26 and/or dilator 28 to the left ventricle 5 and large enough when in the second or expanded/inflated position to be advanced through the cusps 4 and chordae 8 of the mitral valve 3 to reduce the potential of damaging the heart 1 and/or getting entangled within the mitral valve 3. For example, the shaft 50 may have an outer diameter of approximately 0.062" (e.g., a 5 Fr). The messenger balloon 48 may diameter of approximately 0.100" in the first position and a diameter of approximately 15 mm to approximately 20 mm cm in the second position with a length of approximately 8 to approximately 10 mm.

Figure 10:
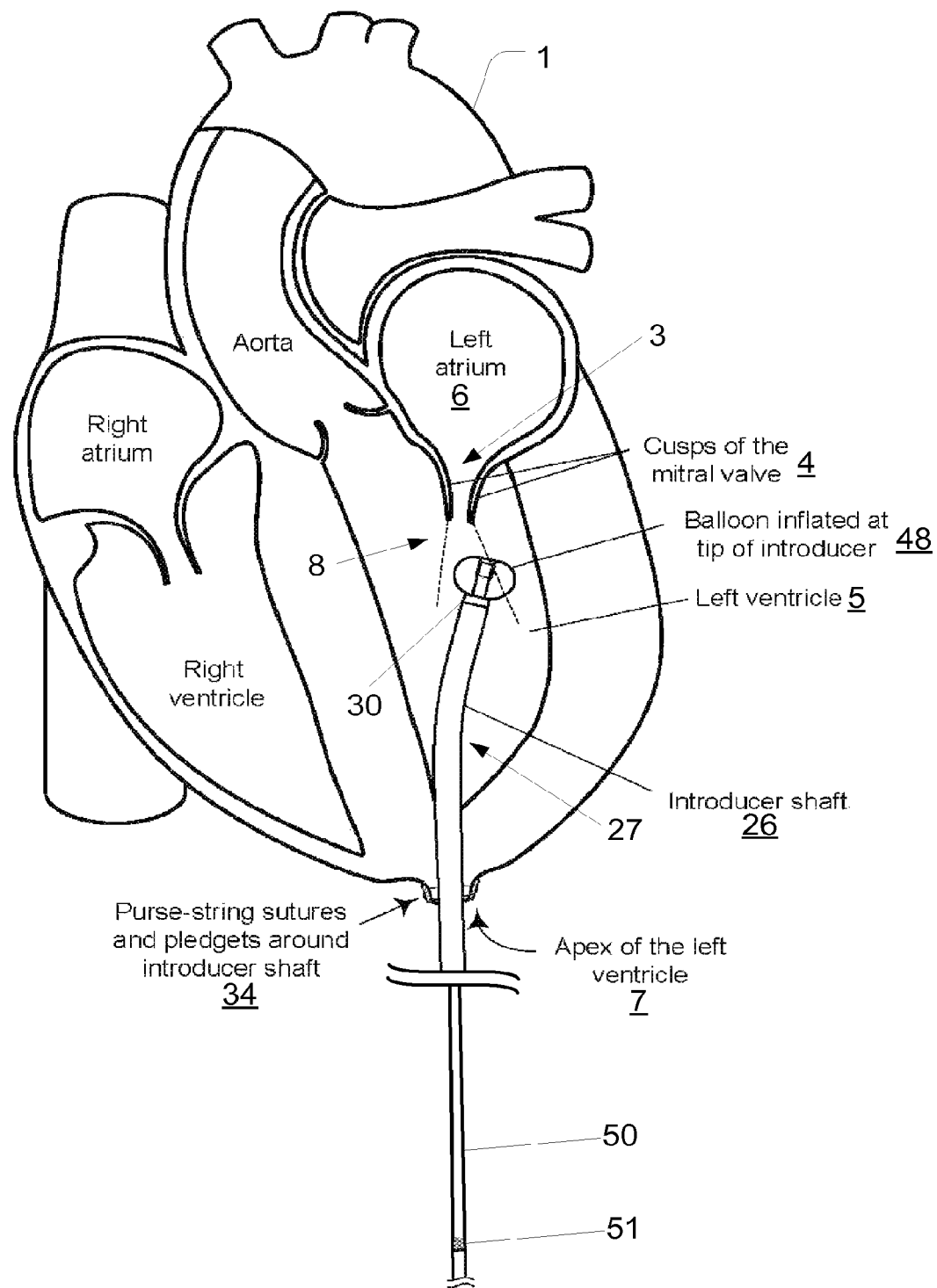
FIG. 10 generally illustrates the inflated messenger balloon being advanced through the mitral valve.
Figure 11:
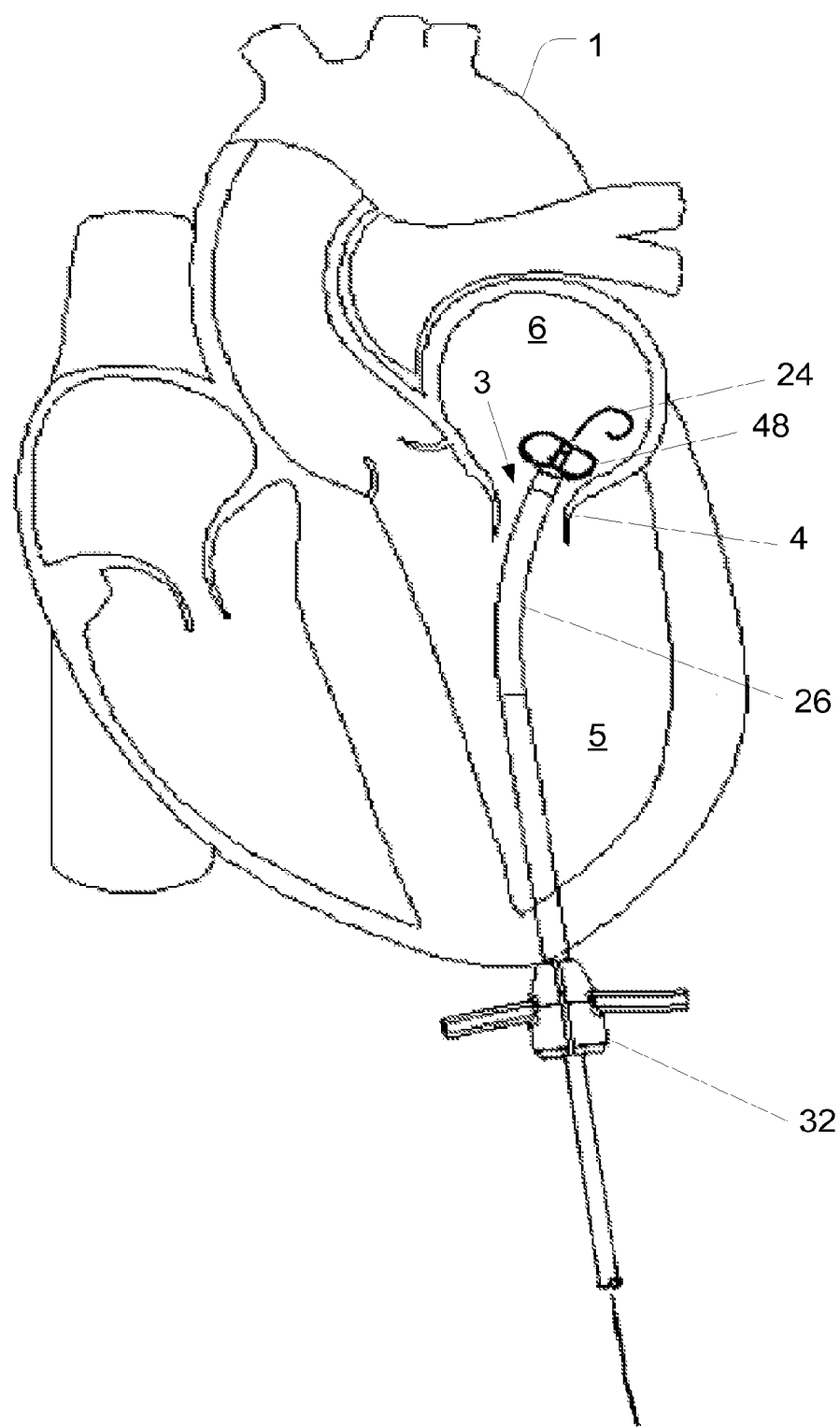
FIG. 11 generally illustrates the inflated messenger balloon in the left atrium

The messenger balloon 48 is advanced towards the mitral valve 3 as generally illustrated in FIG. 10. As can be seen, the bend 27 in the introducer 26 helps to get the introducer 26 correctly orientated spatially, to find the space between the two papillary muscles and avoid the chordae. As noted above, the limitations of the two-dimensional figures do not completely convey the advantage of the bend 27. With the messenger balloon 48 proximate to the mitral valve 3, the messenger balloon 48 may be advanced through the mitral valve 3. The backflow from the left ventricle 5 through the mitral valve 3 into the left atrium 6 (even for a normal mitral valve) helps "pull" the inflated messenger balloon 48 into the mitral space such that the messenger balloon 48 may ultimately be advanced into the left atrium 6 as generally illustrated in FIG. 11. The introducer 26 and the dilator 28 may then be advanced over the shaft 50 of the messenger balloon 48 into the left atrium 6.

Figure 12:
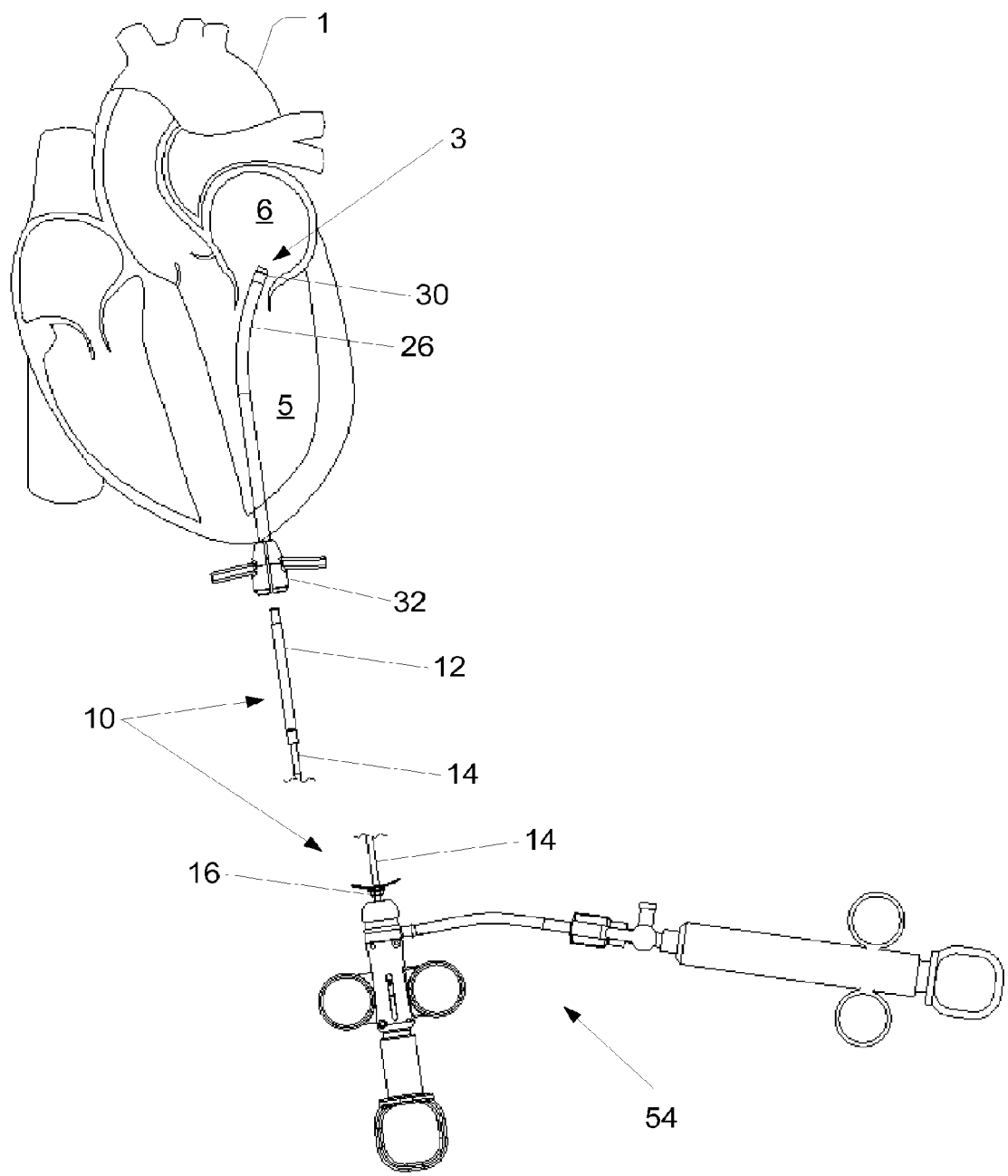
FIG. 12 generally illustrates the implant being loaded into the introducer.

Once the introducer 26 has been advanced through the mitral valve 3 into the left atrium 6, the dilator 28, guide wire 24, and the messenger balloon 48 may be removed from the introducer 26 and the retracted/deflated implant 10 may be loaded into the introducer 26 (for example, through the splitter 32) as generally illustrated in FIG. 12. Prior to loading the implant 10 into the introducer 26, the implant 10 may be de-aired. If entrapped air from the implant 10 is allowed to be introduced into the patient's cardiovascular system, the air may travel to the patient's brain or other parts of the patient's body where it may cause serious bodily harm and/or death (for example, due to blood clotting or the like). To de-air the implant 10, a fluid (such as, but not limited to, a saline solution or the like) may be injected through the inflation lumen 66 into the spacer cavity 68 to flush away and/or remove any entrapped air before the implant 10 is inserted into the introducer 26.

As note previously, the implant 10 includes an expandable spacer 12, a shaft 14, and an anchor assembly 16. When the implant 10 is loaded into the introducer 26, the shaft 14 may have a length substantially longer than the length of the shaft 14 when the implant 10 is secured to the heart 1 (e.g., as shown in FIG. 1). For example, the shaft 14 may be long enough to allow the surgeon to manipulate the implant 10 from outside of the patient's body while the implant 10 is disposed within the left atrium 6/mitral valve 3. The shaft 14 may include generally flexible tubing such as, but not limited to, a poly(tetrafluoroethylene) (PTFE) tube defining an lumen. Optionally, the exterior surface of the shaft 14 may include a fabric sheath or the like configured to prevent blood clots from becoming dislodged off the shaft 14. The shaft 14 may also optionally include one or more stiffeners (not shown) to provide the necessary amount of rigidity to the shaft 14 such that the shaft 14 is able to maintain the position of the spacer 12 with respect to the mitral valve 3 when installed. The stiffener may include, for example, braided mesh or the like.

Figure 13:
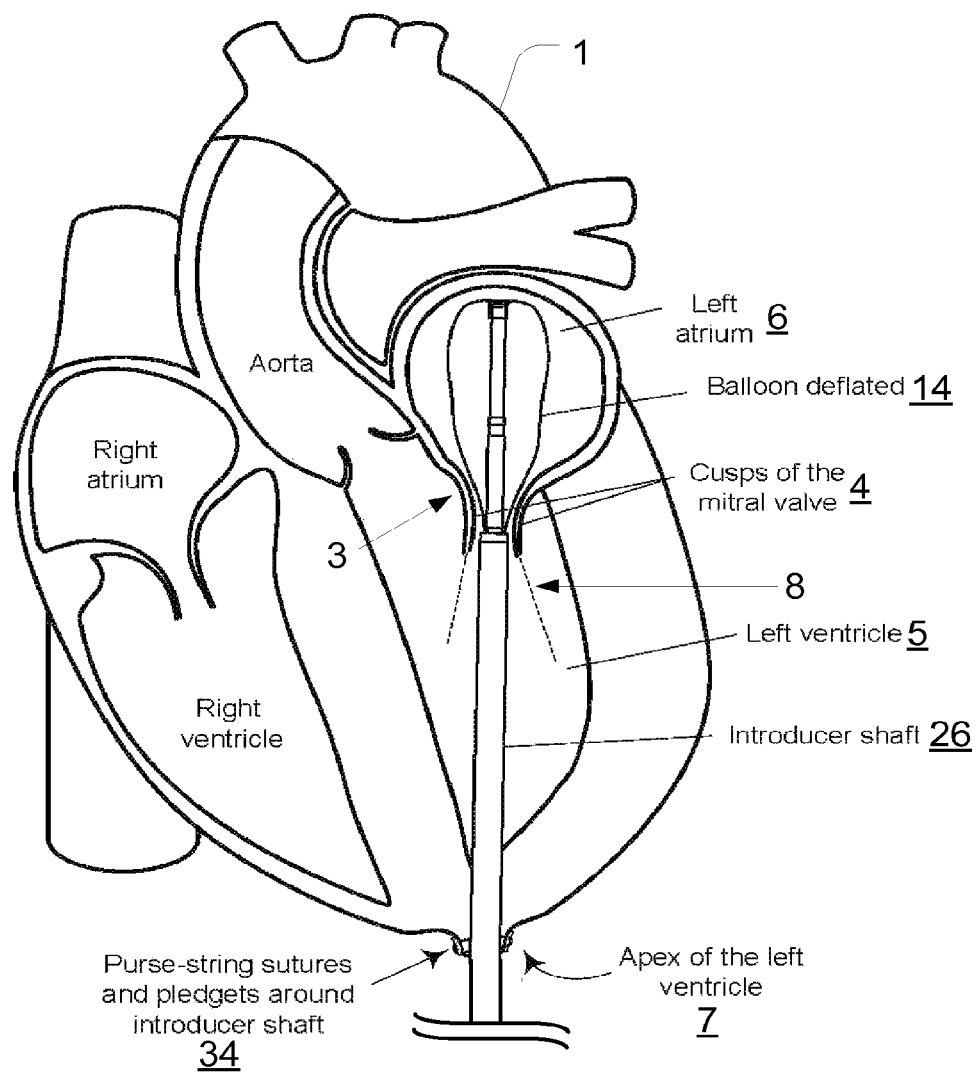
FIG. 13 generally illustrates the implant in the left atrium.
Figure 14:
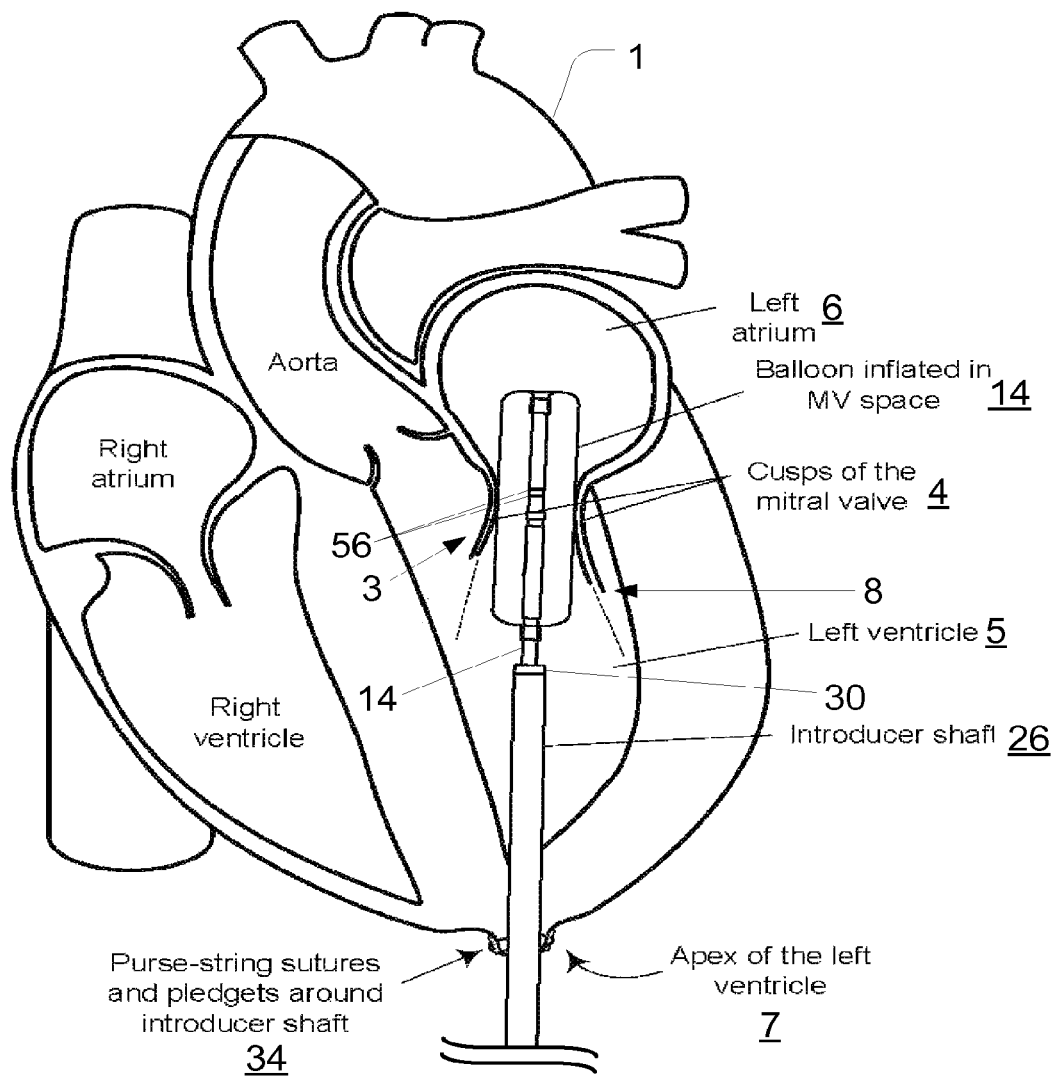
FIG. 14 generally illustrates the implant in the mitral valve.

According to one embodiment, the shaft 14 is secured to a handle assembly 54 and the anchor assembly 16 may disposed proximate to the handle assembly 54. The handle assembly 54 may be used to advance the implant 10 through the introducer 26 until at least a portion of the implant 10 (e.g., the retracted/deflated spacer 12) protrudes beyond the distal end 30 of the introducer 26 in the left atrium 6 as generally illustrated in FIG. 13. Once a portion of the spacer 12 protrudes beyond the distal end 30 of the introducer 26, the introducer 26 may be retracted slightly to allow the rest of the spacer 12 to protrude beyond the distal end 30. The spacer 12 may also be inflated using the handle assembly 54 and pulled back from the left atrium 6 and into the annulus of the mitral valve 3 as generally illustrated in FIG. 14. The position of the spacer 12 within the annulus of the mitral valve may be determined using one or more markers 56 (e.g., radio-opaque markers which may be visible under fluoroscopy). The distal end 30 of the introducer 26 is now disposed in the left ventricle 5. Contrast medium can be injected into the introducer 26, to the left ventricle 5 to verify if the mitral regurgitation has been significantly reduced by the action of the spacer 12 engaging with the cusps 4 of the mitral valve 3.

Figure 15:
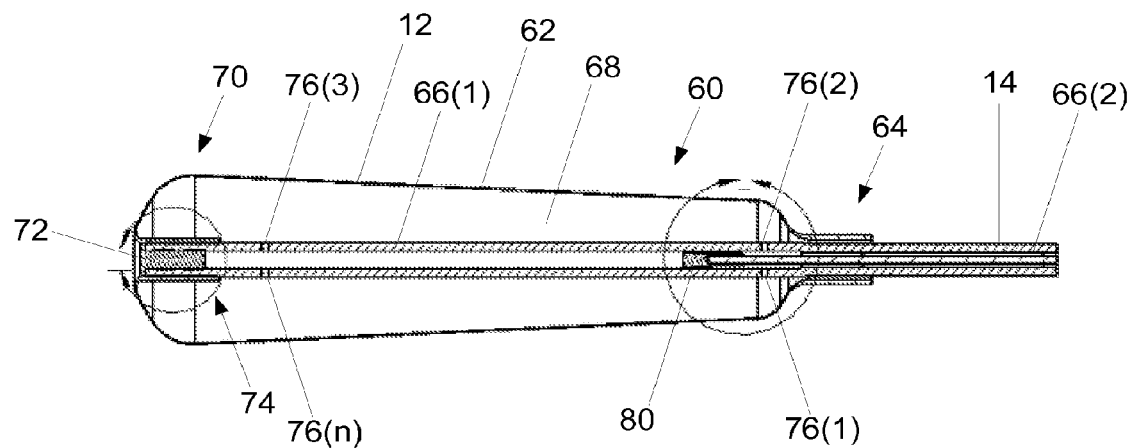
FIG. 15 generally illustrates the implant in a retracted position prior to filling.
Figure 16:
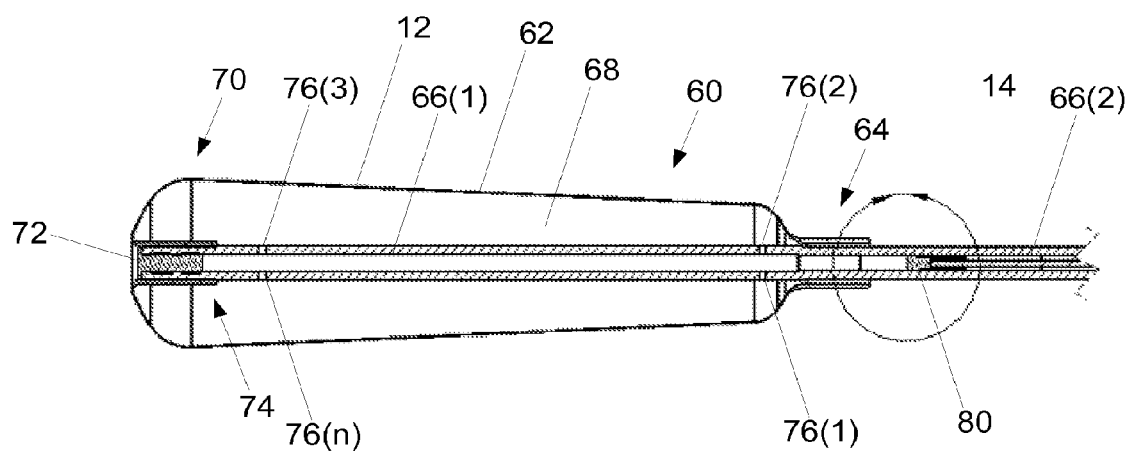
FIG. 16 generally illustrates the implant in an expanded position after filling.

Turning now to FIGS. 15 and 16, the spacer valve assembly 60 of the implant 10 is generally illustrated in a retracted position (FIG. 15) in which the spacer 12 is ready to be expanded (i.e., ready to receive an expansion medium) and in an expanded position (FIG. 16) in which the spacer 12 has been expanded and sealed. The spacer valve assembly 60 allows the spacer 12 to be selective expanded and/or deflated to desired pressure or stiffness. The spacer 12 includes a resilient flexible wall 62 formed from a biologically acceptable material, for example, Elast-Eon™ material or the like.

A first (proximal) end 64 of the wall 62 is coupled, mounted, or otherwise secured to a portion of the shaft 14. The spacer 12 may include a first inflation lumen 66(1), which may extend substantially along substantially the entire longitudinal axis of the spacer 12 or only a portion thereof. The first inflation lumen 66(1) is fluidly couple to a second inflation lumen 66(2) associated with the shaft 14 and is configured to allow an expansion medium (such as, but not limited to, saline or the like) into a spacer cavity 68 from the handle assembly 54 (the handle assembly 54 may be seen, e.g., in FIG. 12). The first inflation lumen 66(1) may be a component of the spacer 12 and/or may include an extension of the shaft 14 (e.g., the first and second inflation lumens 66(1), 66(2) may be parts of the same lumen).

The spacer cavity 68 is defined by the first inflation lumen 66(1) and the wall 62. The second (distal) end 70 of the spacer 12 includes an end plug 72 configured to seal the distal end 74 of the second portion of the first inflation lumen 66(1) to the wall 62. The first inflation lumen 66(1) also includes a plurality of apertures 76(1)-(n). The apertures 76(1)-(n) may be disposed along the length of the first inflation lumen 66(1) and are configured to allow the expansion medium to flow from the first inflation lumen 66(1) into the spacer cavity 62. The first inflation lumen 66(1) may include a first set of apertures (e.g., apertures 76(1), 76(2)) which are disposed proximate to the first end 62 of the spacer 12 and/or a second set apertures (e.g., apertures 76(3), 76(n)) which are disposed proximate to the second end 70 of the spacer 12. The use of two sets of apertures allows for more even inflation of the spacer cavity 68.

As noted herein, the spacer valve assembly 60 is configured to allow the surgeon to selectively expand/retract the spacer 12, and more specifically, the spacer cavity 68. The spacer valve assembly 60 may feature a plunger 80 disposed within first and/or second inflation lumens 66(1), 66(2) which is configured to selectively seal the first inflation lumen 66(1) and/or the apertures 76(1)-(n) and selectively allow the expansion medium to flow into and/or out of the spacer cavity 68.

Figure 18:
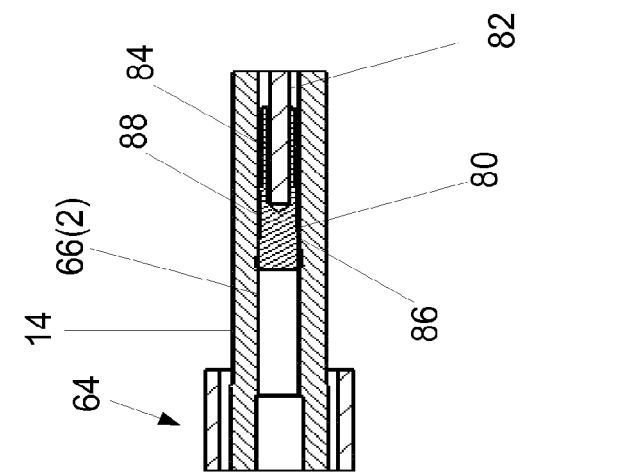
FIG. 18 generally illustrates the spacer valve assembly in an expanded position after filling.
Figure 19:
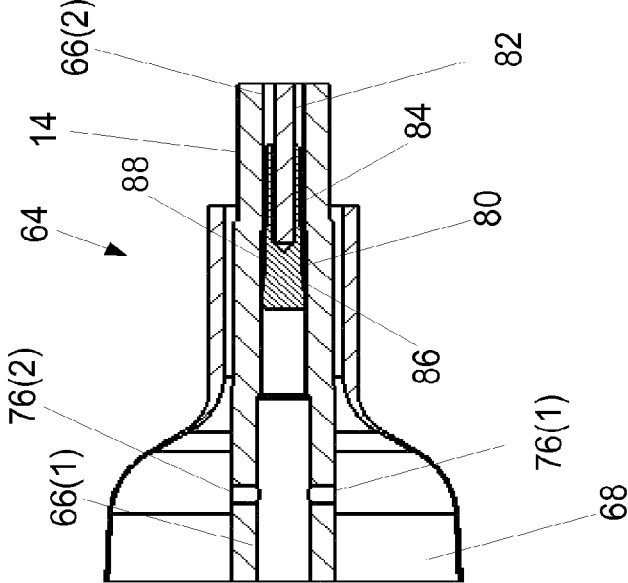
FIG. 19 generally illustrates the spacer valve assembly in an intermediate position.
Figure 17:
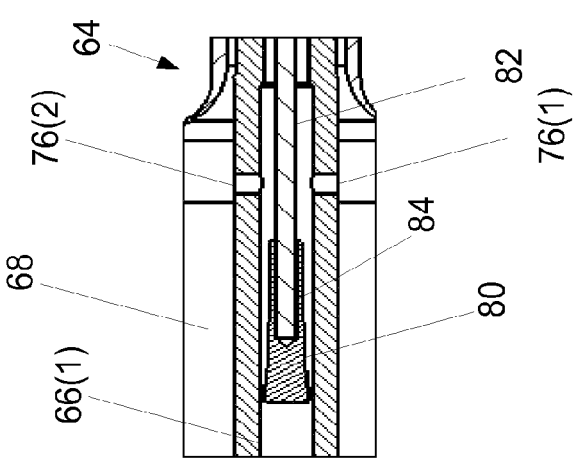
FIG. 17 generally illustrates one embodiment of a spacer valve assembly in a retracted position prior to filling.

With reference to FIGS. 17-19, various positions of the plunger 80 within the first and/or second inflation lumens 66(1), 66(2) are generally illustrated. In particular, FIG. 17 illustrates the plunger 80 in the retracted position ready to be expanded corresponding to FIG. 15. FIG. 18 illustrates the plunger 80 in the expanded, sealed position corresponding to FIG. 16. FIG. 19 illustrates the plunger 80 in an optional, intermediate position in which the spacer cavity 68 is selectively, removably sealed such that the expansion of the spacer cavity 68 within the mitral valve 3 can be verified. The intermediate position allows the surgeon to selectively seal and unseal the plunger 80 such that the surgeon can to be selectively expanded and/or retracted the spacer cavity 68 based on the performance of the implant 10 within the mitral valve 3.

The plunger 80 is coupled to a plunger wire 82. The plunger wire 82 extends through the inflation lumens 66(1), 66(2) of the spacer 12 and/or the shaft 14 and may be coupled to an inflation handle assembly as described herein. The plunger wire 82 allows the surgeon to move the plunger within the first and/or second inflation lumens 66(1), 66(2) into any of the inflation/sealing positions. The plunger wire 82 may be releasably coupled to the plunger wire 82, for example, using a threaded connection 84 or the like.

With reference to FIG. 17, the plunger 80 is in the expansion position ready to be expanded and the apertures 76(1)-(n) are fluidly coupled to the first and second inflation lumens 66(1), 66(2). The plunger 80 may be disposed within the first inflation lumen 66(1) between the first set of apertures 76(1), 76(2) and the second set of apertures 76(3), 76(n). Because the first set of apertures 76(1), 76(2) are upstream of the plunger 80, the first set of apertures 76(1), 76(2) are fluidly coupled to the inflation lumen 66(1). The first inflation lumen 66(1) may have a tapered internal diameter which expands along the longitudinal axis of the spacer 12 from first or proximal end 64 towards the second or distal end 70 of the spacer 12. At least a portion of the cross-section (e.g., the diameter) of the first inflation lumen 66(1) is larger than the cross-section (e.g., diameter) of the plunger 80 such that fluid can flow past the plunger 80, thereby fluidly coupling the second set of apertures 76(3), 76(n) to the inflation lumen 66(1).

Turning now to FIG. 18, the plunger 80 is in the retracted/sealed position in which the apertures 76(1)-(n) are fluidly sealed from the first and second inflation lumens 66(1), 66(2). The plunger 80 may be disposed within and sealed with the first or second inflation lumen 66(1), 66(2) upstream of first and second sets of apertures 76(1)-(n). As such, no expansion medium can flow into or out of the apertures 76(1)-(n) and the spacer cavity 68 is sealed. For the sake of clarity, the plunger 80 will be described as sealing with the second inflation lumen 66(2), however, it should be appreciated that the plunger 80 may seal with either the first and/or the inflation lumens 66(1), 66(2).

The plunger 80 may have a tapered 84 (e.g., a generally cylindrical taper) configured to create a frictional connection (e.g., a Morse taper or the like) with the corresponding taper 86 (e.g., a generally cylindrical taper) of the second inflation lumen 66(2) to seal the second inflation lumen 66(2), and ultimately the spacer cavity 68. The plunger 80 may also form a threaded connection with the second inflation lumen 66(2) to seal the second inflation lumen 66(2), and ultimately the spacer cavity 68. Alternative embodiments of sealing the plunger 80 with the second inflation lumen 66(2) are also possible.

FIG. 19 illustrates the plunger 80 in an optional, intermediate position. When the plunger 80 in the intermediate position, the surgeon may selectively sealed and unseal the spacer cavity 68 to allow the spacer 12 to be expanded further or retracted. The intermediate position may be used when verifying the performance of the spacer 12 within the mitral valve 3. To seal the spacer cavity 68, the plunger 80 is urged distally such that a portion of the plunger 80 seals against the tapered inflation lumen 66(1), 66(2) at a position which is upstream of the apertures 76(1)-(n). To unseal the spacer cavity 68 (e.g., in the event that the surgeon wants to release some of the expansion medium from the spacer cavity 68 to reduce the overall size of the spacer 12), the surgeon urges the plunger 80 proximally. The increasing taper in of the inflation lumen 66(1), 66(2) allows for the expansion medium to flow past the plunger 80 thereby fluidly coupling the apertures 76(1)-(n) to the inflation lumen 66(1), 66(2). In this manner, the surgeon can easily adjust the size of the spacer 12 based on the performance of the implant 10 within the mitral valve 3.

It should be appreciates that the orientations of taper 86 of the plunger 80 and the taper 88 of the inflation lumen 66 may be switched. Switching the orientations of the tapers 86, 88 would result in urging the plunger 80 in the opposite directions to seal and unseal the spacer cavity 68.

Figure 20:
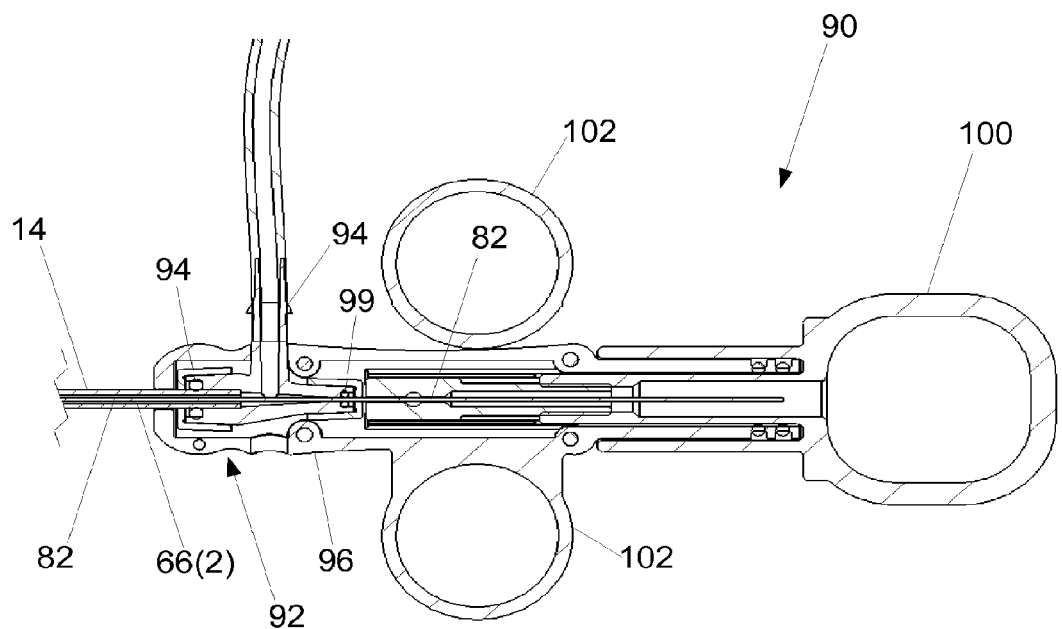
FIG. 20 generally illustrates one embodiment of an inflation handle assembly in a retracted position prior to filling.
Figure 21:
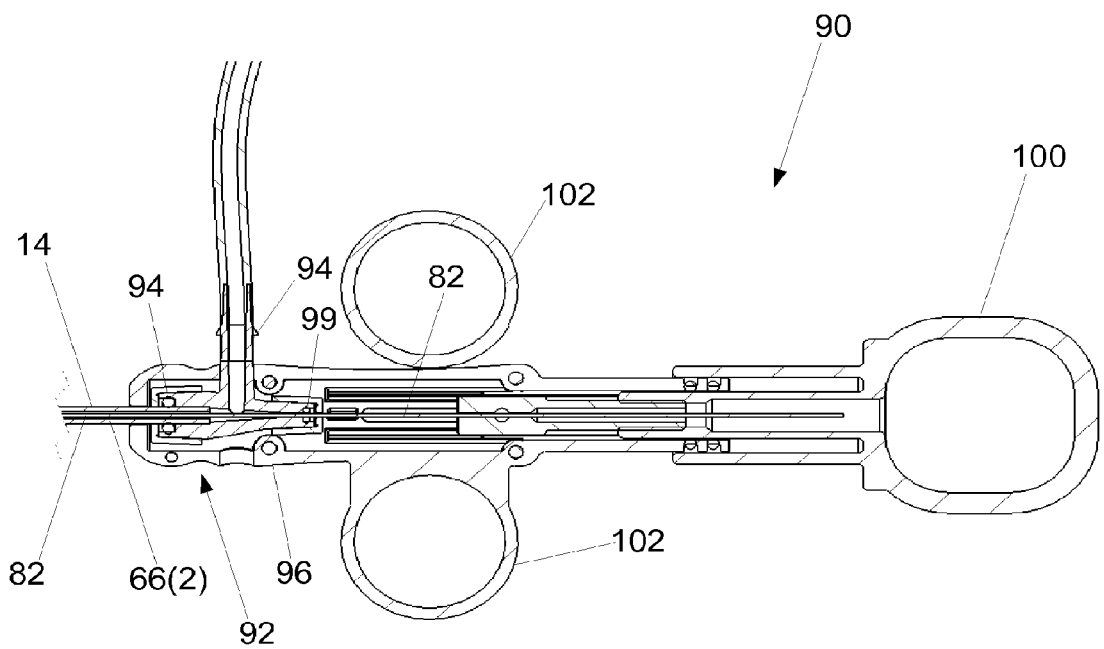
FIG. 21 generally illustrates the inflation handle assembly in an expanded position after filling.

Turning now to FIGS. 20 and 21, one embodiment of an inflation handle assembly 90 is generally illustrated. A proximal end 92 of the shaft 14 may be secured (either permanently or releasably secured) to a portion of the inflation handle assembly 90. For example, the shaft 14 may be hermetically sealed and coupled to inflation handle assembly 90 using one or more seals 94. The body 96 of the inflation handle assembly 90 includes an inflation port 98 which is fluidly coupled to the inflation lumen 66(2) of the shaft 14. The inflation port 98 is configured to be secured to an inflation source (e.g., but not limited to, a plunger/syringe or the like, not shown) for providing the expansion medium to the spacer cavity 68 as described herein.

The plunger wire 82 extends from the inflation lumen 66(2) of the shaft 14 and passes through the body 96 of the inflation handle assembly 90. One more seals 99 may be provided to seal the body 96 to the plunger wire 82 as the plunger wire 82 passes through the body 96. The proximal end of the plunger wire 82 is optionally secured to a translator 100. The translator 100 (which may include a ring, slide, knob, or the like) may be configured to move with respect to the body 96 to push or pull the plunger wire 82 within the inflation lumens 66(1), 66(2). For example, when the translator 100 is in the position illustrated in FIG. 20, the plunger 80 may be arranged in the inflation position as generally illustrated in FIGS. 15 and 17. When the translator 100 is in the position illustrated in FIG. 21, the plunger 80 may be arranged in the expanded, sealed position as generally illustrated in FIGS. 16 and 18. When the translator 100 is in a position between FIGS. 20 and 21, the plunger 80 may be arranged in the intermediate position as generally illustrated in FIG. 19.

The inflation handle assembly 90 may optionally include one or more handle features 102 extending from the body 96 that are configured to facilitate handling of the inflation handle assembly 90 with one hand. For example, the inflation handle assembly 90 may include two handle features 102 disposed on generally opposite sides of the body 96, each of which is configured to receive a different one of a user's fingers (for example, the pointer and middle fingers, respectively). The translator 100 may feature a ring configured to receive a user's thumb. With this arrangement, the surgeon may grip the inflation handle assembly 90 with a single hand and translate the translator 100 back and forth to urge the plunger wire 82 (and ultimately the plunger 68) back and forth to selectively seal and unseal the spacer cavity 68. This arrangement allows the surgeon to control the inflation medium source using the surgeon's other hand.

Figure 22:
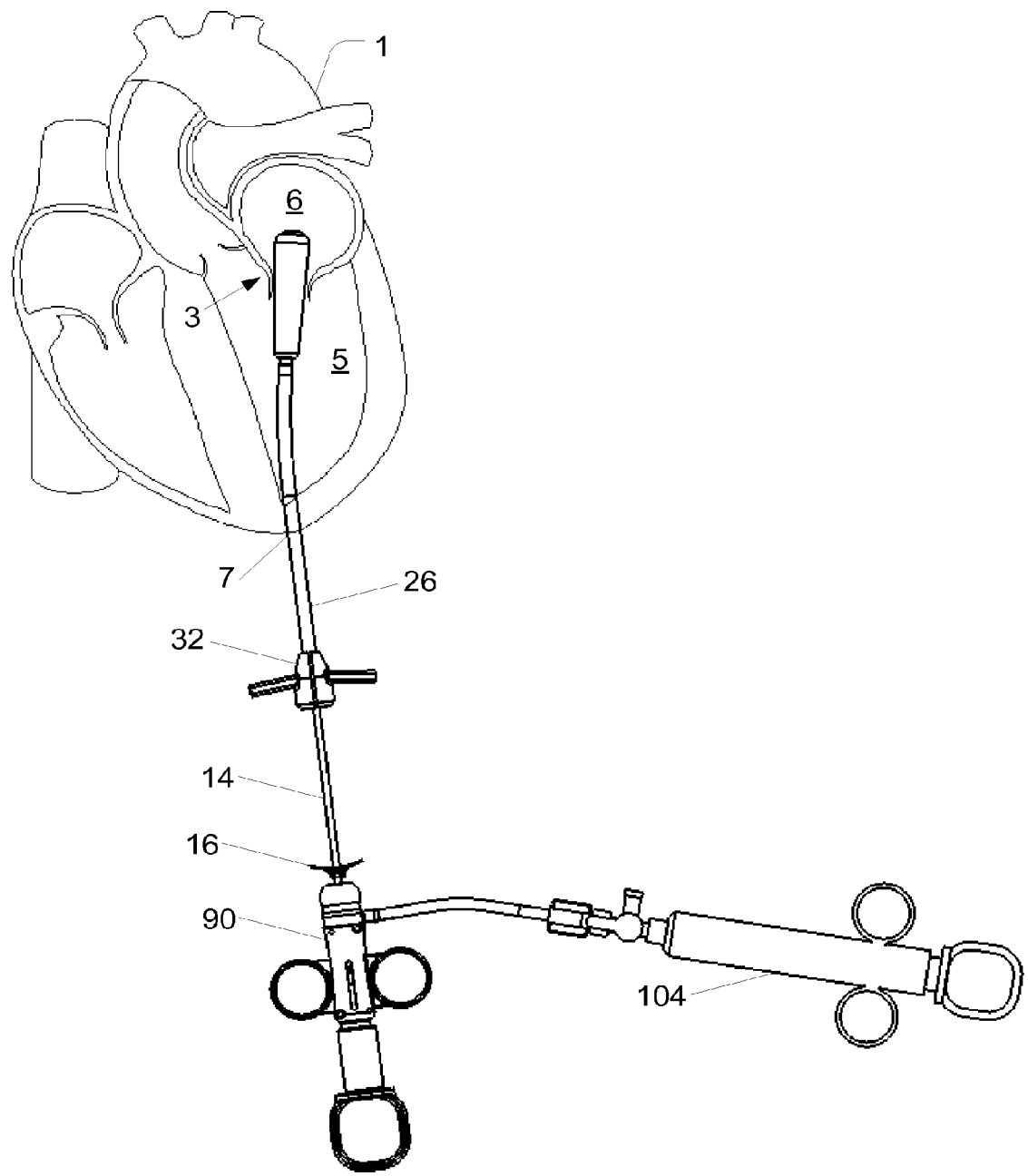
FIG. 22 generally illustrates the implant in the mitral valve, the inflation handle assembly, and a splitter.

Turning now to FIG. 22, the implant 10 is illustrated with the spacer 12 within the heart 1. The shaft 14 of the implant 10 is disposed within the introducer 26 (e.g., a split catheter) and coupled to the inflation handle assembly 90. The anchor 16 is also shown disposed proximate to the inflation handle assembly 90. The inflation port 98 is fluidly coupled to an expansion medium source 104 (e.g., a plunger/syringe). The surgeon may use the inflation handle assembly 90 to manipulate the implant 10 such that the spacer 12 is disposed within the mitral valve 3. The spacer 12 may also be expanded to the desired size using the inflation handle assembly 90 and the expansion medium source 104. The spacer 12 may be sealed using the inflation handle assembly 90 once the desired size of the spacer 12 is determined.

Figure 23:
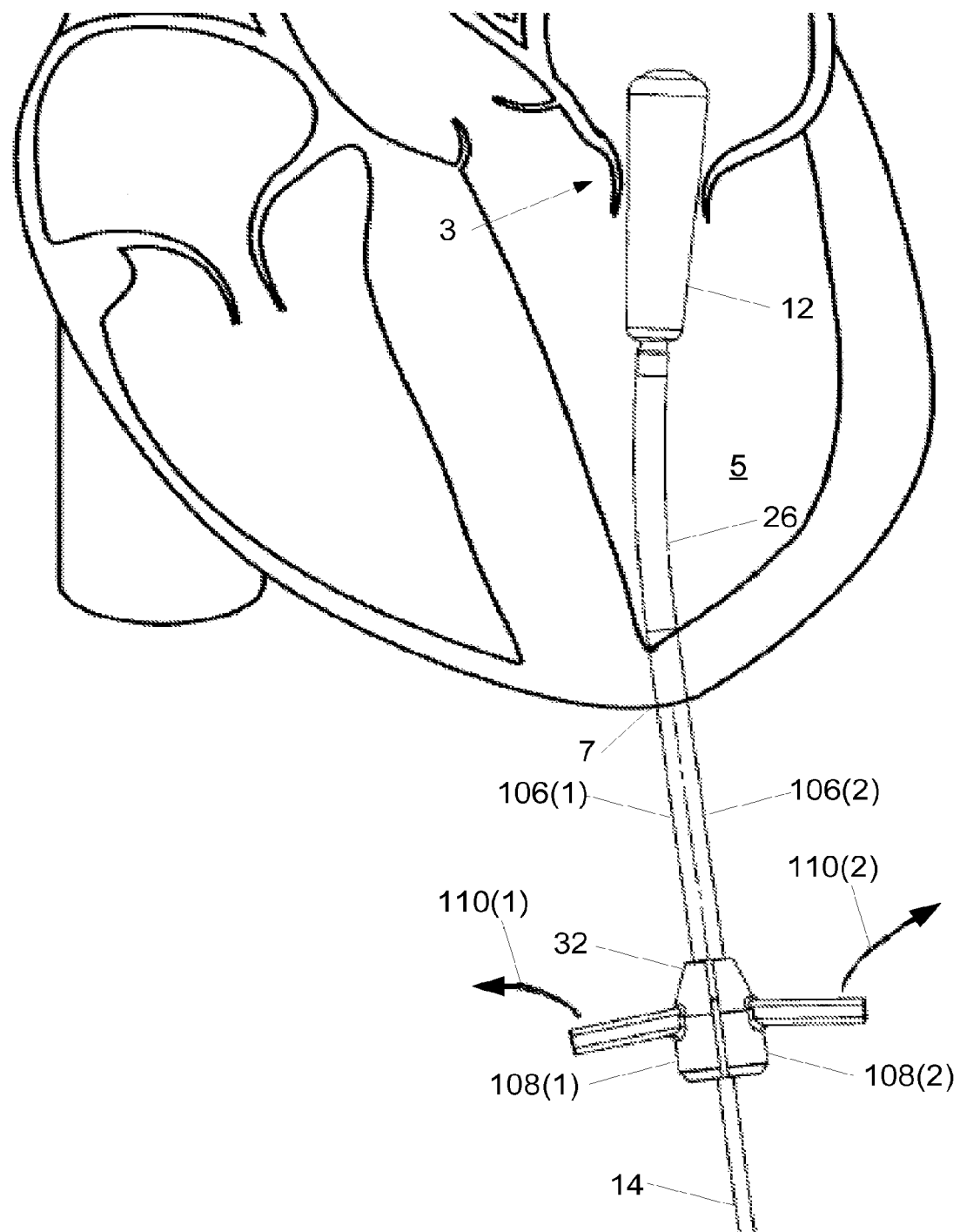
FIG. 23 generally illustrates splitting the introducer after the implant has been verified in the mitral valve.
Figure 24:
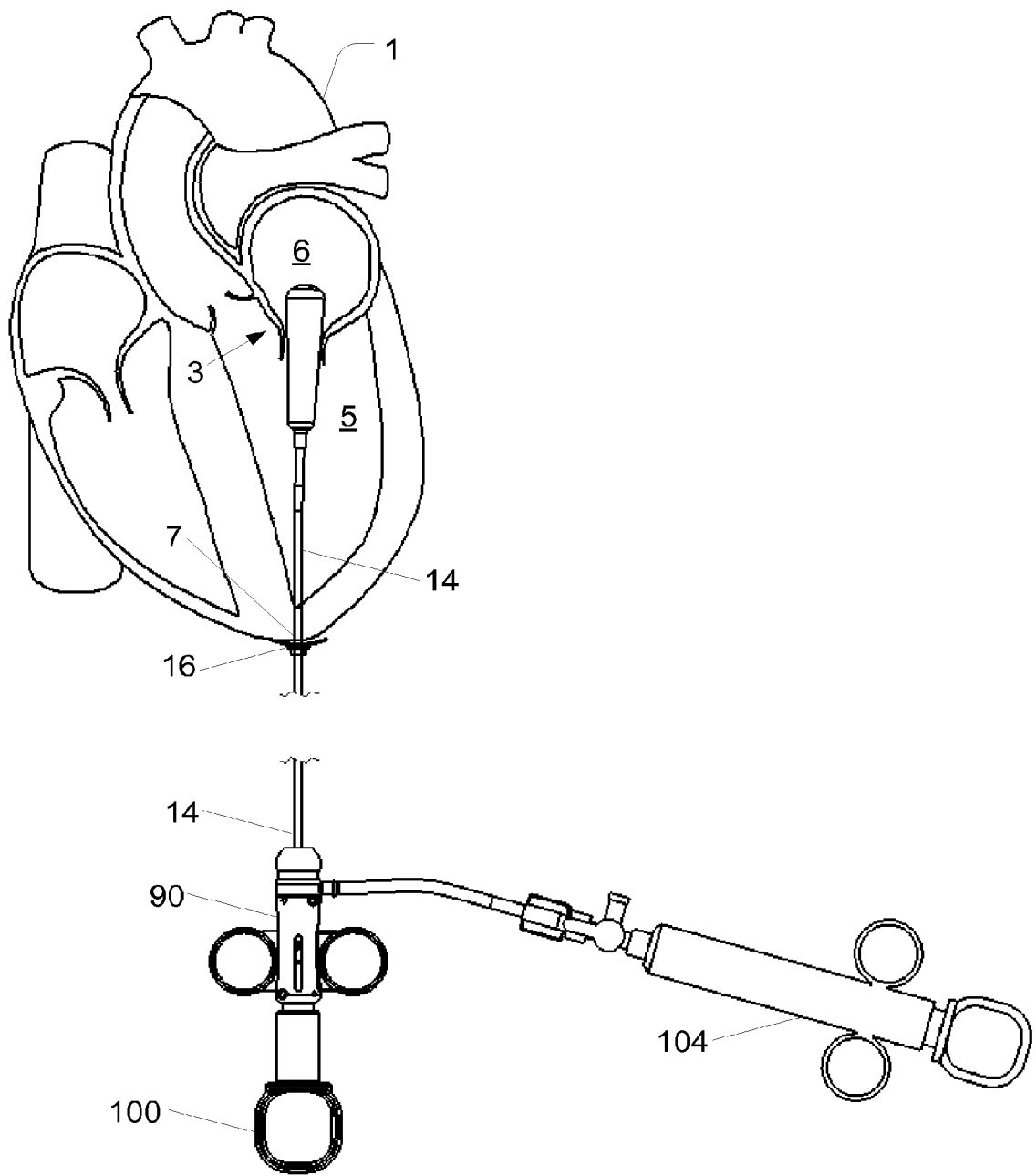
FIG. 24 generally illustrates implant in the mitral valve with the anchor assembly advanced to the apex.
Figure 25:
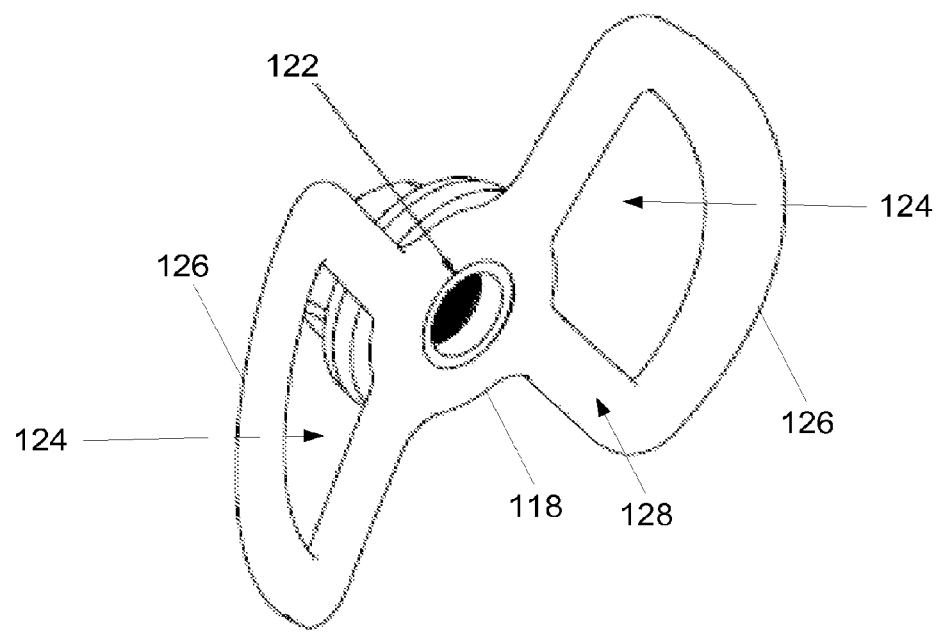
FIGS. 25-28 generally illustrate various views of one embodiment of the anchor assembly.

After the operation of the spacer 12 has been verified and the spacer has been sealed, the introducer 26 may be removed from the shaft 14, for example, as generally illustrated in FIG. 23. For example, the splitter 32 may be used to split the introducer 26 into two or more pieces 106(1), 106(2) along its length, for example, by pulling the two halves 108(1), 108(2) generally in the directions of arrows 110(1), 110(2). As the introducer 26 is split, the introducer 26 may be retracted from heart 1 through the incision in the apex 7. The purse string sutures 34 (not shown for clarity) may also be tightened as the introducer 26 is removed from the incision in the apex 7 to minimize blood loss. Once the introducer 26 has been removed from the shaft 14, the anchor assembly 16 may be advanced along the shaft 14 until the anchor assembly 16 is adjacent to and/or abuts against the apex 7 of the heart 1, for example as generally illustrated in FIG. 24. Additionally, the plunger wire 82 may be disconnected from the plunger 80, for example, by rotating the translator 100 to unthread the plunger wire 82 from the plunger 80.

Figure 26:
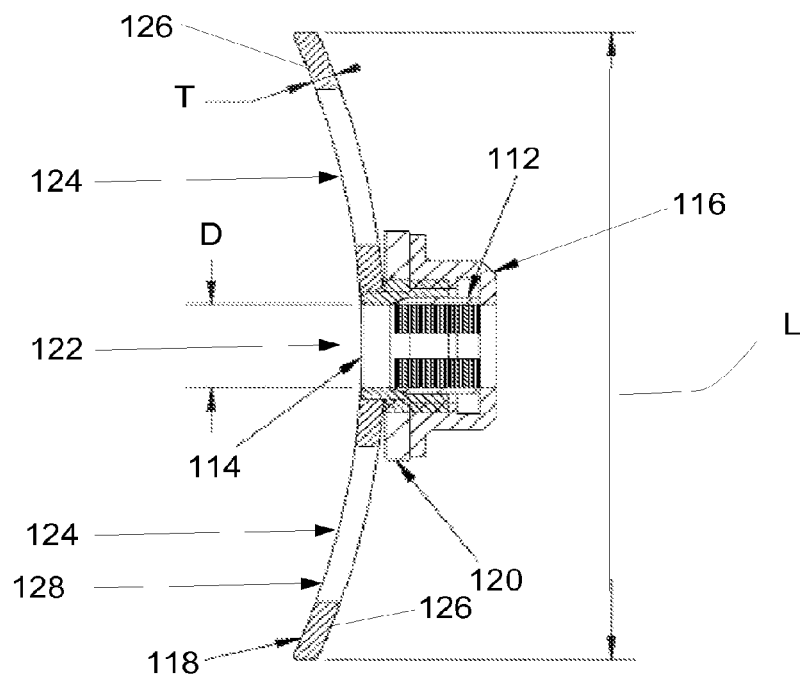
Figures 27, 28:
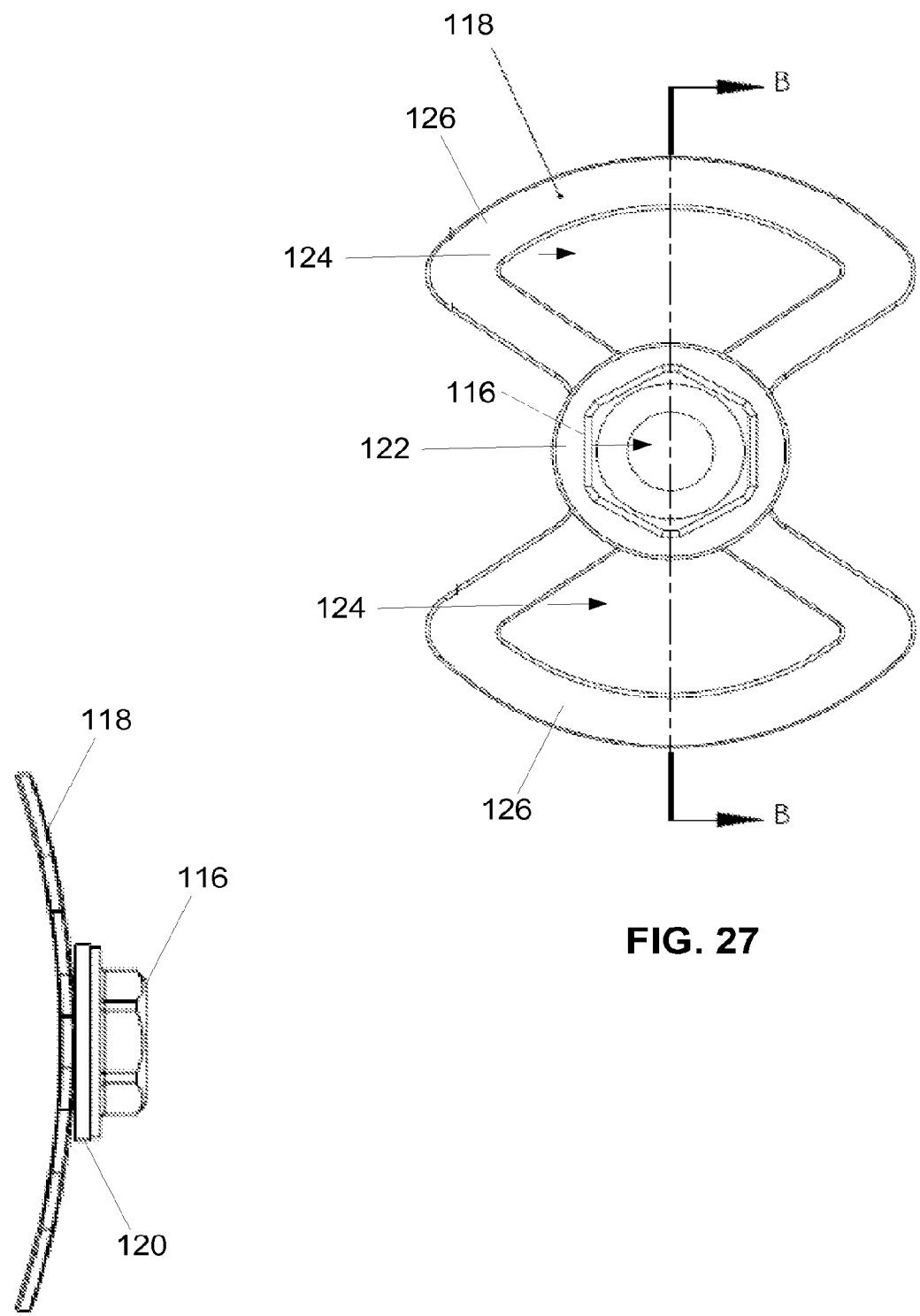

Turning now to FIGS. 25-28, various views of one embodiment of an anchor assembly 16 are generally illustrated. The anchor assembly 16 (as best seen in FIG. 26 which is a cross-sectional view taken along line B-B of FIG. 27) includes a clamp ring 112, a collar 114, a nut 116, an anchor support 118, and optionally a felt pad 120. The anchor assembly 16 defines a passageway 122 extending therethrough which is configured to receive and be advanced over the shaft 14 of the implant 10. The clamp ring 112, collar 114, and nut 116 are configured to define a compression fitting around a perimeter of the shaft 14, thereby securing the anchor assembly 16 to the shaft 14. In particular, once the anchor assembly 16 is in place (e.g., abutting against the tissue surround the incision site proximate to the apex 7), the surgeon holds the anchor support 118 while rotating the nut 116, thereby compressing the clamp ring 112 and the collar 114 to apply a radially compressive force against the shaft 14. The radially compressive force secures the anchor assembly 16 to the shaft 14. For illustrative purposes, the anchor support 118 may have a length L of 0.875 cm and thickness T of 0.030 cm, and the passageway 122 may have a diameter D of 0.116 cm.

To secure the anchor assembly 16 to the heart 1, the anchor support 118 may be sutured to the heart tissue. The anchor support 118 may include one or more openings 124 and/or arms 126 over which one or more sutures (not shown for clarity) may be passed to stitch the anchor support 118 to the heart tissue, and secure the anchor assembly 16. The mounting surface 128 of the anchor support 118 may have a curvature which substantially corresponds to the curvature of the heart tissue proximate to the incision site about the apex 7. The anchor support 118 may optionally be coated/covered/wrapped with pledget material. The pledget material facilitates tissue to growth over the anchor support 118, thereby further enhancing the connection between the anchor assembly 16 and the heart 1.

Other anchor assemblies can be used to secure the implant 10 to the heart 1. For example, a one or more prongs, barbs, staples, clamps, and/or helical screws can be used to secure the implant 10 to the heart. Additionally, the anchor assembly 16 may be eliminated. For example, the implant 10 may be secured to the heart using the shaft 14 which may curl and secured to the heart 1, for example, using sutures, staples, or the like.

With reference now to FIG. 1, the implant 10 is shown secured to the heart 1. Once the anchor assembly 16 is secured to the heart 1, the shaft 14 may be cut proximate to the anchor assembly 16. When installed, the spacer 12 is configured to interact and/or cooperate with (e.g., engage) at least a portion of the native mitral valve 3 (e.g., the cusps 4) to reduce and/or eliminate excessive regurgitation. As such, the configuration and/or geometries of the spacer 12 may depend upon the particulars of the condition of the patient's mitral valve 3 and the damage thereto. In addition, the implant 10 (e.g., the spacer 12 and/or the shaft 14) has sufficient overall rigidity to maintain the spacer 12 within the mitral valve 3 such that the implant 10 performs as intended.

According to one aspect, the present disclosure features a trans-apical implant. The implant includes a spacer defining spacer cavity configured to be expanded from a retracted position, a shaft extending from the spacer, the shaft defining an inflation lumen fluidly coupled to the spacer cavity and configured to be fluidly coupled to an expansion medium source, and a spacer valve assembly disposed within at least one of the spacer or shaft, the spacer valve assembly configured to allow selectively allow an expansion medium to flow into the spacer cavity to be selectively expand the spacer from a retracted position to an expanded position.

According to another aspect, the present disclosure features an implant delivery system. The implant delivery system includes an introducer having at least one lumen and an implant. The implant is configured to be received in the lumen and includes a spacer and a shaft. The spacer defines spacer cavity configured to be expanded from a retracted position while disposed within the lumen of the introducer. The shaft is configured to extend from the spacer and defines an inflation lumen fluidly coupled to the spacer cavity and configured to be fluidly coupled to an expansion medium source.

According to yet another aspect, the present disclosure features a method of trans-apically delivering an implant within a heart. The implant includes a shaft and a spacer configured to interact with at least a portion of at least one cusp of a mitral valve to at least partially restrict a flow of blood through the heart valve in a closed position. The method includes trans-apically advancing an introducer through an incision in an apex of the heart into a left ventricle; advancing the introducer through the mitral valve into a left atrium; advancing the implant through a lumen, defined by the introducer, into the left atrium, wherein the shaft extends within the lumen from the spacer and beyond the incision in the heart; introducing an expansion medium through the shaft to expand the spacer; locating the spacer within the mitral valve to reduce mitral regurgitation; removing the introducer from the heart; and securing the implant to an external surface of the heart proximate to the apex.

As mentioned above, the present disclosure is not intended to be limited to a system or method which must satisfy one or more of any stated or implied object or feature of the present disclosure and should not be limited to the preferred, exemplary, or primary embodiment(s) described herein. The foregoing description of a preferred embodiment of the present disclosure has been presented for purposes of illustration and description. It is not intended to be exhaustive or to limit the present disclosure to the precise form disclosed. Obvious modifications or variations are possible in light of the above teachings. The embodiment was chosen and described to provide the best illustration of the principles of the present disclosure and its practical application to thereby enable one of ordinary skill in the art to utilize the present disclosure in various embodiments and with various modifications as is suited to the particular use contemplated. All such modifications and variations are within the scope of the present disclosure as determined by the claims when interpreted in accordance with breadth to which they are fairly, legally and equitably entitled.

What is claimed:
1. An implant comprising:
an expandable spacer having a resilient flexible wall and defining a spacer cavity configured to be expanded from a retracted position to an expanded position;

a shaft extending from said spacer, said shaft defining an inflation lumen fluidly coupled to said spacer cavity and configured to be fluidly coupled to an expansion medium source; and an anchor assembly configured to be advanced over said shaft and secured to a portion thereof, said anchor assembly further configured to be secured to an exterior surface of a patient's heart.

2. The implant of claim 1, wherein said anchor assembly comprises a compression fitting configured to apply a radially compressive force against said shaft to secure said anchor assembly to said shaft.

3. The implant of claim 2, wherein the compression fitting comprises a clamp ring, a collar and a nut.

4. The implant of claim 2, wherein said anchor assembly further comprises an anchor support defining at least one arm over which a suture is stitched.

5. The implant of claim 4, wherein said anchor assembly further comprises a pledget material disposed on at least one arm.

6. The implant of claim 1, further comprising a spacer valve assembly disposed within at least one of said spacer or shaft, said spacer valve assembly configured to selectively allow an expansion medium to flow into said spacer cavity to selectively expand, to flow out of said spacer cavity to selectively deflate said spacer, or a combination thereof.

7. The implant delivery system of claim 6, wherein said spacer valve assembly further comprises a plunger configured to be slidably disposed within said inflation lumen, wherein said plunger, when in a first position, is configured to allow said expansion medium to flow into or out of said spacer cavity, and when in a second position, said plunger is configured to seal said spacer cavity.

8. The implant of claim 7, wherein plunger is coupled to a plunger wire extending through said inflation lumen in said shaft and beyond a proximal end of said shaft, wherein said plunger wire is configured to selectively move said plunger within said inflation lumen.

9. The implant of claim 8, wherein said plunger wire is threadedly coupled to said plunger.

10. The implant of claim of claim 6, further comprising an inflation handle assembly comprising an inflation port fluidly coupled to said inflation lumen.

11. The implant of claim 10, wherein said inflation port is configured to be secured to an inflation source.

12. The implant of claim 11, wherein the inflation source is selected from the group consisting of a plunger and a syringe.

13. An implant delivery system comprising:
an introducer including at least one lumen;
an implant configured to be received in said lumen, said implant comprising an expandable spacer and a shaft; and
an anchor assembly configured to be advanced over said shaft and secured to a portion thereof, said anchor assembly further configured to be secured to an exterior surface of a patient's heart;
wherein said spacer comprises a resilient flexible wall and defines a spacer cavity configured to be expanded from a retracted position to an expanded position, and
wherein said shaft extends from said spacer and defines an inflation lumen fluidly coupled to said spacer cavity and configured to be fluidly coupled to an expansion medium source.

14. The implant delivery system of claim 13, wherein said anchor assembly comprises a compression connection configured to apply a radially compressive force against said shaft to secure said anchor assembly to said shaft.

15. The implant delivery system of claim 13, wherein said anchor assembly further comprises an anchor support defining at least one arm over which a suture is stitched.

16. The implant delivery system of claim 13, wherein said anchor assembly further comprises a pledget material disposed on at least one arm.

17. The implant delivery system of claim 13, further comprising a spacer valve assembly disposed within at least one of said spacer or shaft, said spacer valve assembly configured to selectively allow an expansion medium to flow into said spacer cavity to selectively expand, to flow out of said spacer cavity to selectively deflate said spacer, or a combination thereof.

18. The implant delivery system of claim 17, wherein said spacer valve assembly further comprises a plunger configured to be slidably disposed within said inflation lumen, wherein said plunger, when in a first position, is configured to allow said expansion medium to flow into or out of said spacer cavity, and wherein said plunger, when in a second position, is configured to seal said spacer cavity.

19. The implant delivery system of claim of claim 13, further comprising an inflation handle assembly comprising an inflation port fluidly coupled to said inflation lumen and is configured to be secured to an inflation source.

* * * * *